(12) United States Patent
Drews et al.

(10) Patent No.: US 9,295,548 B2
(45) Date of Patent: Mar. 29, 2016

(54) GUIDE SHIELDS FOR MULTIPLE COMPONENT PROSTHETIC HEART VALVE ASSEMBLIES AND APPARATUS AND METHODS FOR USING THEM

(75) Inventors: Michael J. Drews, Palo Alto, CA (US); Donnell W. Gurskis, Belmont, CA (US); Mimi Nguyen Fitterer, Redwood City, CA (US); Takashi Harry Ino, San Jose, CA (US); James Hong, Palo Alto, CA (US)

(73) Assignee: Medtronic, Inc., Fridley, MN (US)

( * ) Notice: Subject to any disclaimer, the term of this patent is extended or adjusted under 35 U.S.C. 154(b) by 411 days.

(21) Appl. No.: 11/742,390

(22) Filed: Apr. 30, 2007

(65) Prior Publication Data
US 2007/0260305 A1 Nov. 8, 2007

Related U.S. Application Data

(63) Continuation of application No. 60/746,038, filed on Apr. 29, 2006, which is a continuation of application No. 60/914,742, filed on Apr. 29, 2007.

(51) Int. Cl.
*A61F 2/24* (2006.01)
*A61B 17/04* (2006.01)
*A61B 17/00* (2006.01)

(52) U.S. Cl.
CPC ............... *A61F 2/2427* (2013.01); *A61F 2/243* (2013.01); *A61F 2/2409* (2013.01); *A61F 2/2418* (2013.01); *A61B 17/0469* (2013.01); *A61B 2017/00243* (2013.01); *A61F 2/2412* (2013.01); *A61F 2/2436* (2013.01); *A61F 2/2439* (2013.01); *A61F 2220/0008* (2013.01); *A61F 2220/0033* (2013.01); *A61F 2220/0075* (2013.01); *A61F 2220/0083* (2013.01); *A61F 2230/0006* (2013.01); *A61F 2250/0063* (2013.01); *A61F 2250/0069* (2013.01); *A61F 2250/0091* (2013.01)

(58) Field of Classification Search
None
See application file for complete search history.

(56) References Cited

U.S. PATENT DOCUMENTS

| 5,489,298 | A | * | 2/1996 | Love et al. | 623/2.14 |
|---|---|---|---|---|---|
| 5,716,401 | A | * | 2/1998 | Eberhardt et al. | 623/66.1 |
| 5,984,959 | A | * | 11/1999 | Robertson et al. | 623/2.11 |
| 6,197,053 | B1 | * | 3/2001 | Cosgrove et al. | 623/2.11 |
| 2001/0044656 | A1 | * | 11/2001 | Williamson et al. | 623/2.11 |
| 2004/0030381 | A1 | * | 2/2004 | Shu | 623/2.11 |
| 2005/0137686 | A1 | * | 6/2005 | Salahieh et al. | 623/2.11 |
| 2005/0222674 | A1 | * | 10/2005 | Paine | 623/1.24 |
| 2006/0195184 | A1 | * | 8/2006 | Lane et al. | 623/2.38 |
| 2006/0195185 | A1 | * | 8/2006 | Lane et al. | 623/2.38 |
| 2006/0195186 | A1 | * | 8/2006 | Drews et al. | 623/2.38 |

* cited by examiner

*Primary Examiner* — Yashita Sharma
*Assistant Examiner* — Rebecca Preston

(57) ABSTRACT

A heart valve assembly includes an annular prosthesis and a plurality of guide shields removably attached around a circumference of the annular prosthesis. A plurality of elongate guide rails extend from the annular prosthesis, which are releasably retained by the guide shields. During use, the annular prosthesis is directed into a biological annulus, e.g., with the guide rails retained by the guide shields, and secured to tissue surrounding the biological annulus using fasteners. The guide rails are released from the guide shields, and a valve prosthesis is advanced over the leaders and through a passage defined by the guide shields towards the annular prosthesis. The guide rails may include retentions elements that secure the valve prosthesis to the annular prosthesis. The guide shields are removed from the annular prosthesis, the guide rails are separated from the annular prosthesis, and are removed from the biological annulus.

38 Claims, 14 Drawing Sheets

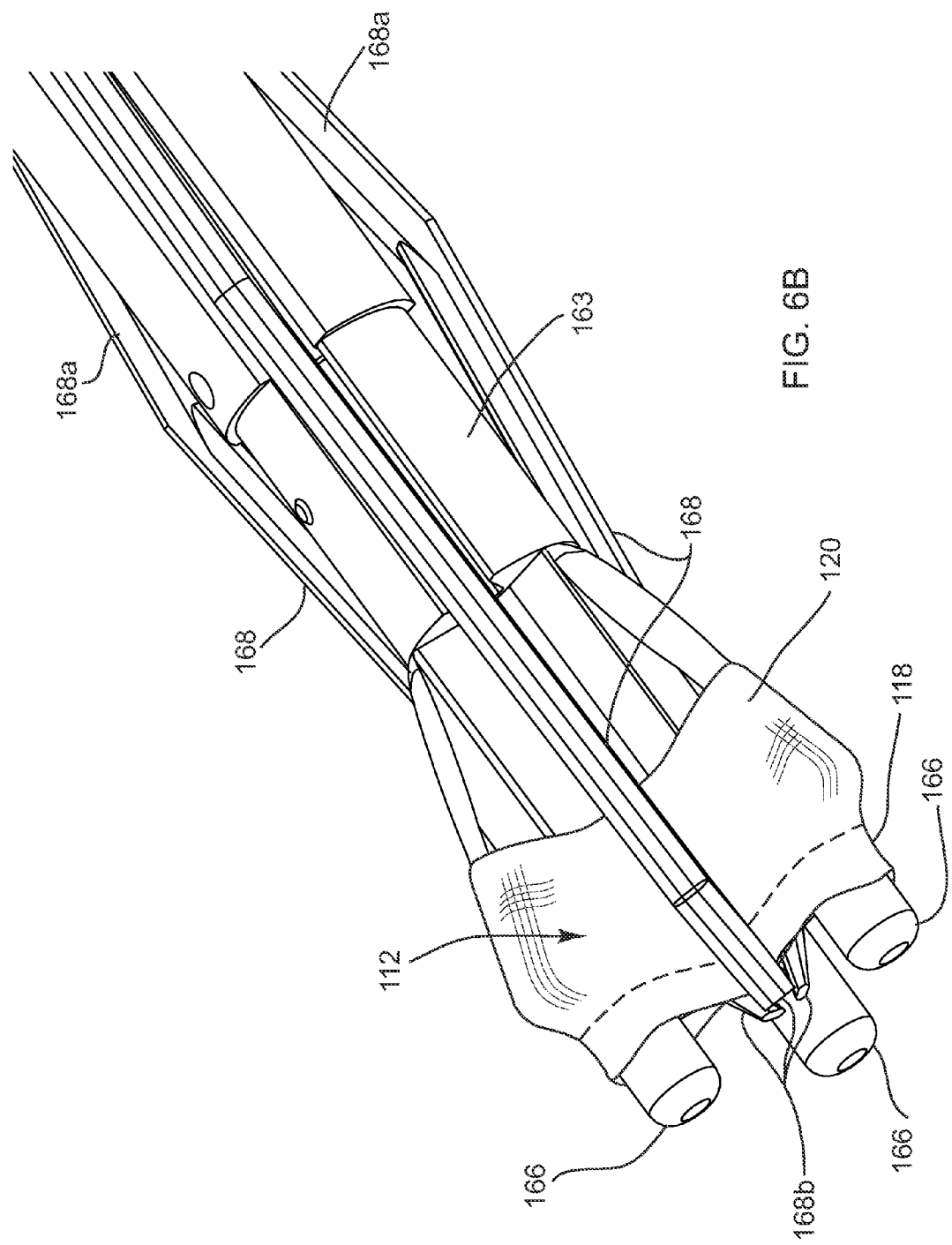

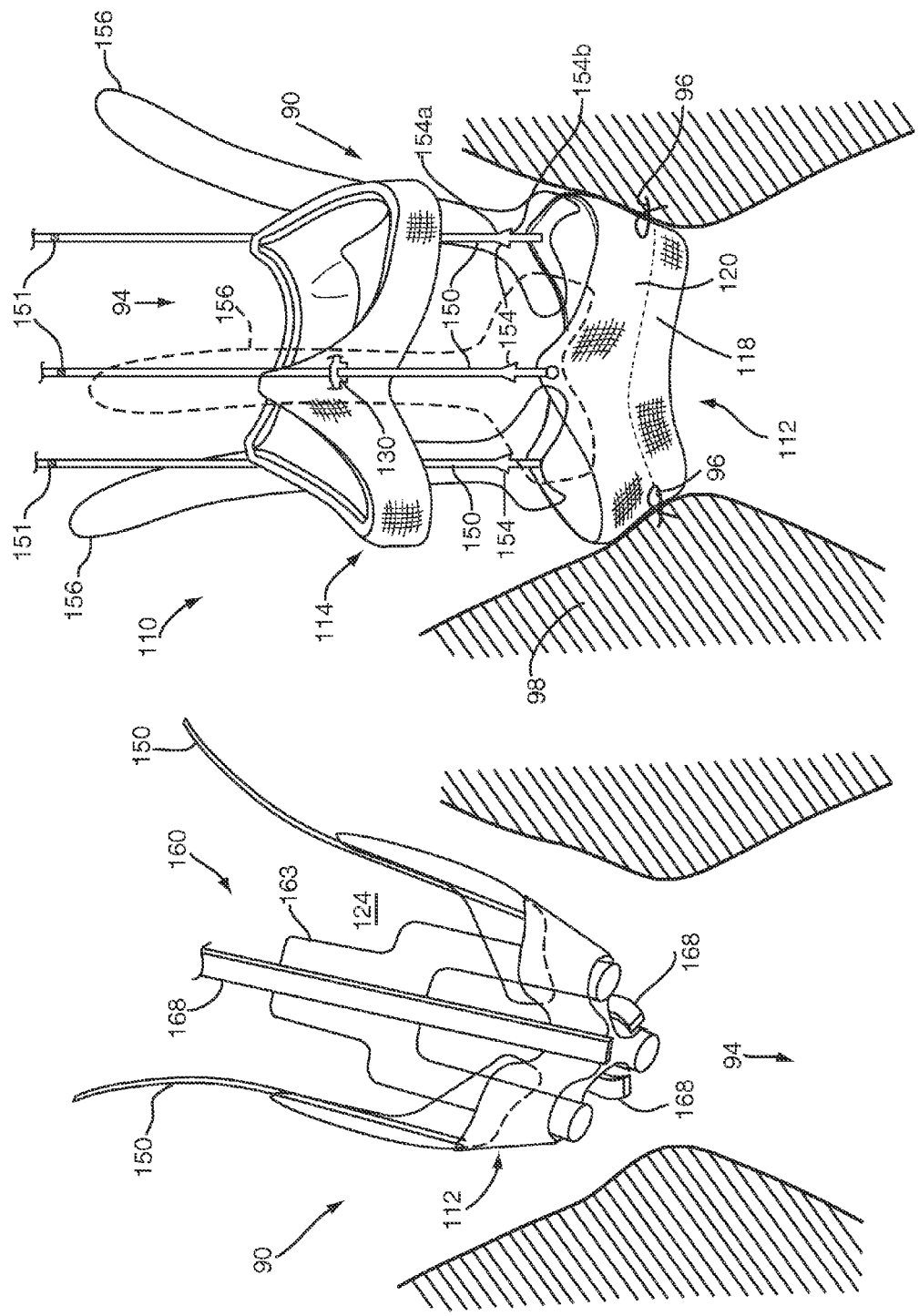

GUIDE SHIELDS FOR MULTIPLE COMPONENT PROSTHETIC HEART VALVE ASSEMBLIES AND APPARATUS AND METHODS FOR USING THEM

RELATED APPLICATION DATA

This application claims benefit of co-pending provisional application Ser. Nos. 60/746,038, filed Apr. 29, 2006, and 60/914,742, filed Apr. 29, 2007, the entire disclosures of which are expressly incorporated by reference herein.

FIELD OF THE INVENTION

The present invention relates generally to heart valves that may be implanted within a patient, and, more particularly, to multiple component heart valve assemblies that may be assembled together, and to apparatus and methods for guiding and/or otherwise facilitating assembly of components of multiple component heart valve assemblies during implantation.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

In addition, less invasive or minimally invasive procedures are often desirable, because they may reduce stress on the patient's body and/or accelerate recovery after a procedure. Such procedures may involve creating smaller access sites and/or even using ports to access a procedure site. During valve replacement, in order to introduce a prosthetic heart valve and/or sewing ring into a patient's heart, the heart must be accessed, e.g., by sternotomy or thoracotomy. The resulting opening must be sufficiently large to permit passage of the prosthetic heart valve and still allow the physician to access and/or observe the site of implantation. Thus, conventional procedures for implanting prosthetic heart valves may not be compatible with less invasive or minimally invasive procedures.

SUMMARY OF THE INVENTION

The present invention is directed to prosthetic heart valves that may be implanted within a patient. More particularly, the present invention is directed to multiple component heart valve assemblies that may be assembled together, and to apparatus and methods for guiding and/or otherwise facilitating assembly and/or implantation of components of multiple component heart valve assemblies. The present invention is also directed to apparatus and methods for assembling components of heart valve assemblies including guides and/or other components.

In accordance with one embodiment, an assembly is provided for receiving a valve prosthesis to replace a natural or prosthetic heart valve within a biological annulus. The assembly may include an annular prosthesis including an annular member implantable within the biological annulus, one or more guide members removably attached to the annular prosthesis for guiding a valve member towards the annular prosthesis, and one or more connectors for securing the valve member relative to the annular prosthesis. In one embodiment, the guide members may be attached to the annulus prosthesis by one or more sutures, and the guide members may be removed from the annular prosthesis by severing one or more of the sutures. For example, a single suture may be cut, thereby allowing the suture(s) to unravel or otherwise allow the guide members to be released from the annular prosthesis. Alternatively, multiple sutures may be provided, but may be collected or combined at a desired location, e.g., near an upper end of the guide members, such that a single cut at the desired location may allow the guide member to be released from the annular prosthesis. Optionally, the suture(s) may remain at least partially attached to the guide members such that the sutures are removed with the guide members from the annular prosthesis and/or patient.

Optionally, the assembly may also include one or more of a sewing cuff extending outwardly from the annular member and/or a collar extending upwardly from the annular member for receiving the valve member. In addition or alternatively, the assembly may include a plurality of elongate guide rails or other leaders extending from the annular prosthesis along which a valve member may be directed. In this alternative, the guide rails may be releasably coupled to the guide members, e.g., through openings in upper ends of the guide members to bias the guide rails outwardly away from a central axis of the assembly, e.g., to improve visualization during the implantation, installation, and/or other surgical procedure.

In accordance with another embodiment, a heart valve assembly is provided for implanting within a biological annulus. The assembly includes a first annular prosthesis including an annular member implantable within a biological annulus, and a second valve prosthesis connectable to the first prosthesis. One or more guide members are removably attached to the first prosthesis for guiding the second prosthesis towards the first prosthesis during implantation. For example, the one or more guide members may include a plurality of guide shields spaced apart around a periphery of the first prosthesis thereby at least partially defining a passage through which the second prosthesis may be directed towards the first prosthesis.

Optionally, the first prosthesis may also include one or more of a sewing cuff extending outwardly from the annular member, a plurality of elongate leaders extending from the annular prosthesis along which the valve member may be directed, and/or a collar extending upwardly from the annular member for receiving the valve member. The second prosthesis may include an annular frame and at least one valve element, e.g., a plurality of tissue leaflets. The first prosthesis and/or the second prosthesis may include one or more connectors for securing the second prosthesis relative to the first prosthesis.

In accordance with yet another embodiment, a system is provided for implanting a valve prosthesis within a biological annulus that includes a first annular prosthesis including an annular member implantable within the biological annulus and one or more guide members or other leaders removably attached to the annular prosthesis, and a delivery tool for carrying the first prosthesis. The delivery tool may include an elongate shaft including a proximal end with a handle, a distal end sized for introduction into the biological annulus, and an actuator for releasably carrying the first prosthesis. Optionally, the tool may include one or more elements for holding the one or more guide members away from a central axis of the first prosthesis to facilitate introducing a prosthetic valve towards the first prosthesis. Optionally, the system may also include a second valve prosthesis that may be guided towards the first prosthesis by the one or more guide members. In this option, the second prosthesis may be carried by the tool carrying the first prosthesis or by a separate tool.

In accordance with still another embodiment, a method is provided for implanting a heart valve assembly within a biological annulus that includes implanting a first prosthesis into the biological annulus, the first prosthesis including one or more guide members extending upwardly therefrom. A second valve prosthesis is advanced towards the first prosthesis, the second prosthesis being guided towards the first prosthesis by the one or more guide members. The one or more guide members are then removed from the first prosthesis, e.g., before or after securing the second prosthesis to the first prosthesis. In an exemplary embodiment, the guide members may be sufficiently long to extend out of the biological annulus and/or the patient's body, and the guide members may facilitate introducing the second prosthesis into the biological annulus. For example, the guide members may allow the second prosthesis to slide along an inner surface of the one or more guide members through any intervening tissue and/or may provide a smooth and/or lubricious surface along which the second prosthesis may slide during placement into the desired anatomical site. Without guide members, the friction between the surface of the second prosthesis and any intervening tissue may be so great as to require higher than desired forces to insert the second prosthesis and/or may cause the intervening tissue to buckle, collapse, and impinge the second prosthesis from reaching the desired final anatomical position within the biological annulus.

Other aspects and features of the present invention will become apparent from consideration of the following description taken in conjunction with the accompanying drawings.

BRIEF DESCRIPTION OF THE DRAWINGS

The drawings illustrate exemplary embodiments, in which:

FIGS. 6A and 6B are end and side views, respectively, of a distal end of the tool of FIGS. 5A-5C, showing the gasket of FIG. 2 (with the guide shields and guide rails omitted for clarity) secured thereto in a folded or contracted condition.

FIGS. 7A-7C are cross-sectional views of a biological annulus, showing a method for implanting a heart valve assembly including the gasket of FIG. 2.

DETAILED DESCRIPTION OF THE EXEMPLARY EMBODIMENTS

Figure 1:
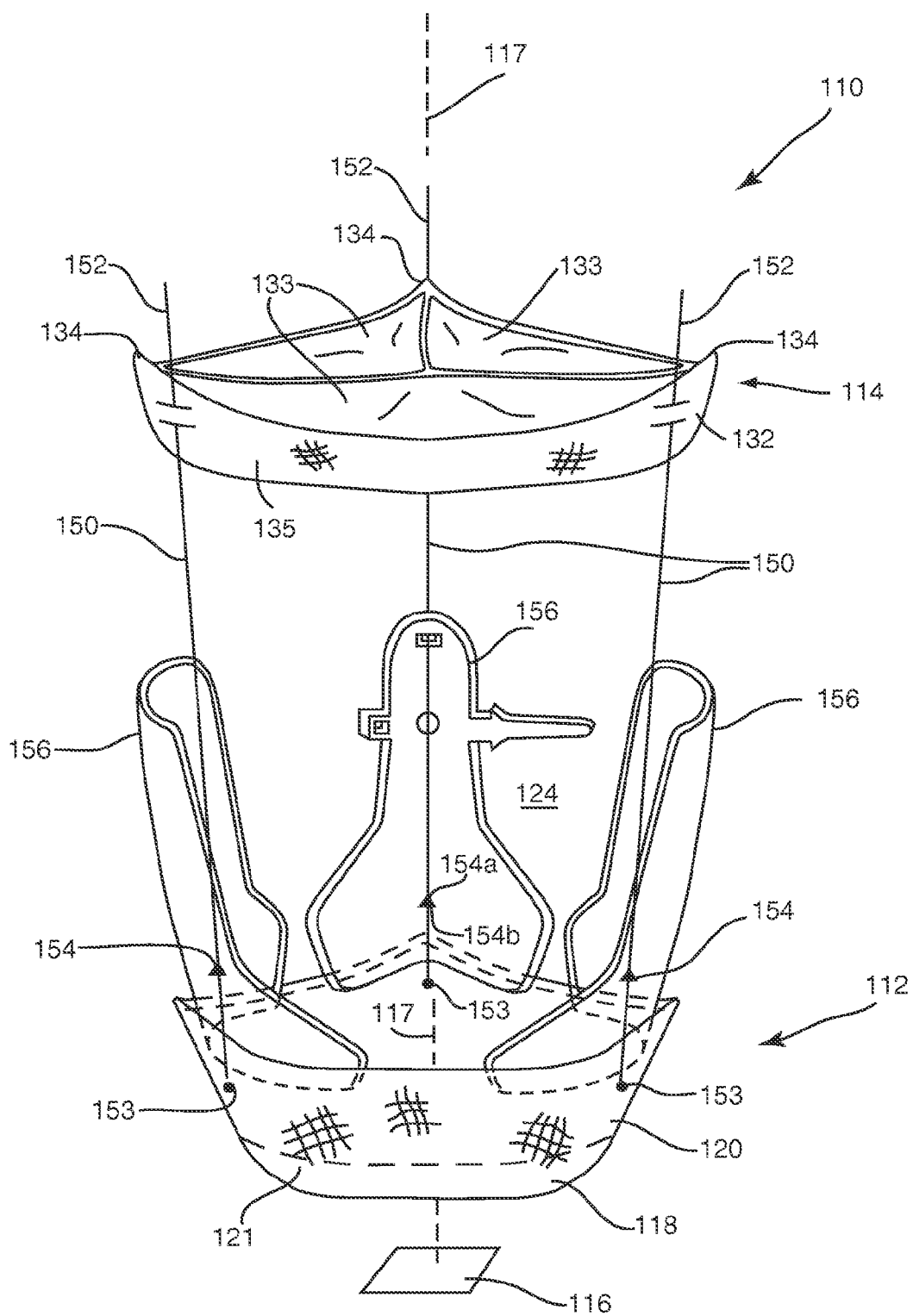
FIG. 1 is a perspective view of a two piece heart valve assembly including a gasket member having a plurality of guide shields extending therefrom and a valve member.
Figure 2:
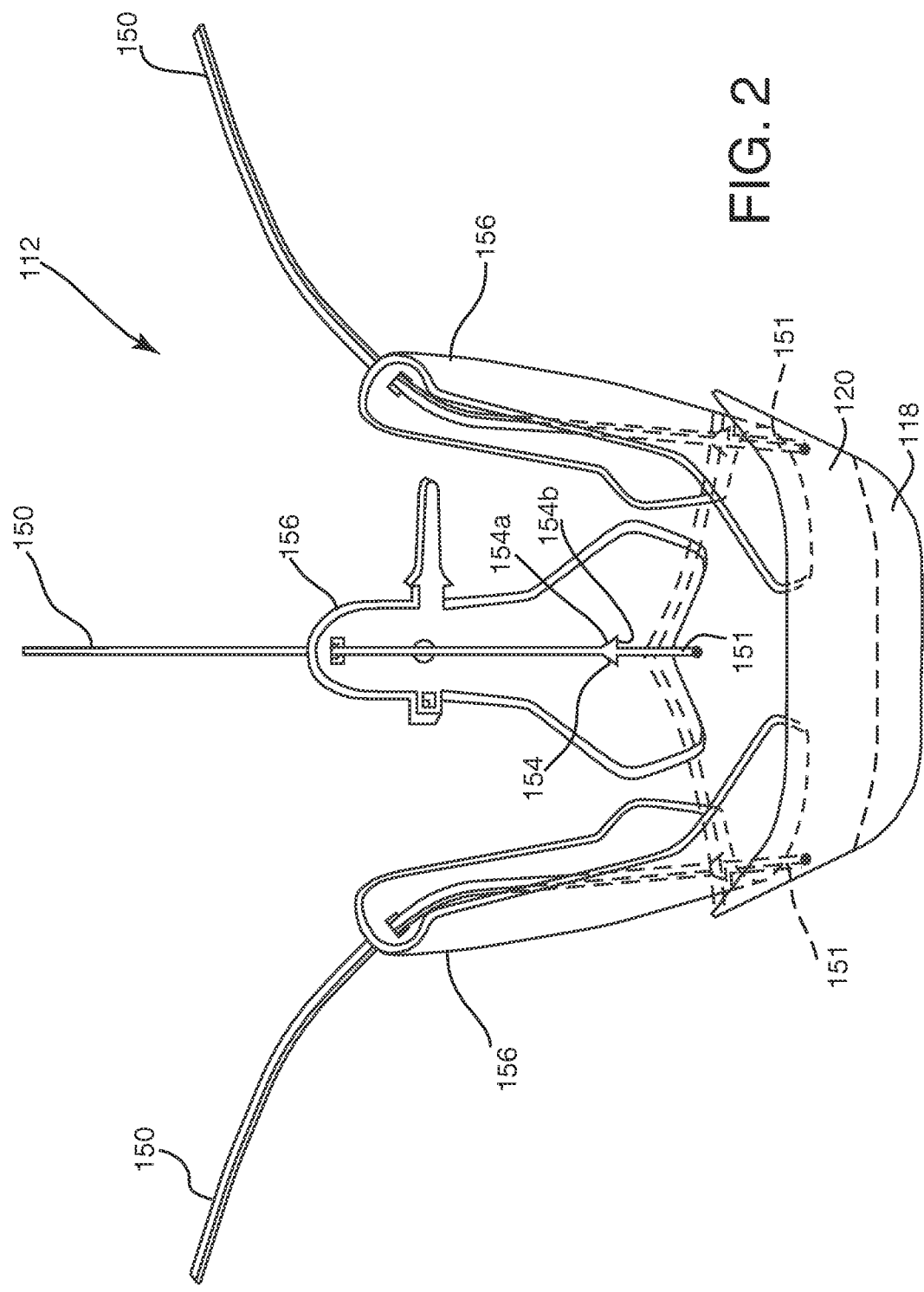
FIG. 2 is a perspective view of a gasket member including an annular prosthesis and a plurality of guide shields and guide rails extending from an annular prosthesis, which may included in the assembly of FIG. 1.

Turning to the drawings, FIGS. 1 and 2 shows an embodiment of a heart valve assembly 110 that generally includes a gasket member 112 and a valve member 114. The gasket member 112 is an annular shaped body generally defining a plane 116 and a central longitudinal axis 117 extending substantially perpendicular to the plane 116. As shown, the gasket member 112 includes an annular ring 118, a sewing cuff 120, a plurality of elongate guide rails, leaders, or other elements 150 extending from the sewing cuff 120 or other portion of the gasket member 112, and a plurality of guide shields 156 removably attached to the gasket member 112. A fabric covering 121 may be provided on one or more components of the gasket member 112, e.g., over the annular ring 118 and/or over a core of the sewing cuff 120, as described further below.

In one embodiment, the annular ring 118 may have a generally circular shape. Alternatively, the annular ring 118 may have a multi-lobular shape about the circumference, e.g., including three lobes separated by scallops or cusps (not shown). The annular ring 118 may be formed from an elastic or superelastic material, for example, metal, such as Nitinol, stainless steel, and the like, a polymer, or a composite material. Such material may facilitate compression and/or expansion of the annular ring 118, as described further below.

In an exemplary embodiment, the annular ring 118 may be cut from a flat sheet of base material having a desired thickness for the annular ring 118, for example, by laser cutting, mechanical cutting, and the like. Thus, the annular ring 118 may be initially formed as a long band of material, having a width corresponding to the desired width of the annular ring 118 and a length corresponding to the desired circumference of the annular ring 118. The band may be wrapped around a mandrel or otherwise restrained in a generally cylindrical shape with the ends adjacent to one another, and the band may be heat treated or otherwise processed to program the generally cylindrical shape into the material to create the annular ring 118. The generally cylindrical shape may include the ends overlapping one another, spaced apart from one another to provide an open "C" shape, or attached to one another. In another exemplary example, the annular ring 18 may be manufactured from a solid rod of material, e.g. Nitinol, stainless steel, a polymer, or composite material, e.g., by machining, electrical discharge machining ("EDM"), laser cutting, or other processes.

Optionally, the annular ring 118 may be heat treated to program a shape memory into the band material, e.g., when the material is in an austenitic state. For example, the programmed shape may be an enlarged or relaxed condition, e.g., having a substantially circular shape. The composition of the material may be such that the annular ring 118 transforms to a substantially martensitic state substantially below body temperature, e.g., at or below ambient temperatures (e.g., 20° C. or less). Thus, in the martensitic state (before delivery), the annular ring 118 may be relatively soft such that the annular ring 118 may be plastically compressed or otherwise deformed, e.g., into a contracted condition to facilitate delivery, as described below. A transition temperature of the material may be set such that the annular ring 118 transforms substantially back to an austenitic state close to or at about body temperature (e.g., 37° C. or more). Thus, once the annular ring 118 is exposed within a patient's body, the annular ring 118 may automatically become biased towards the enlarged condition due the shape memory of the austenitic state.

Alternatively, the material may be programmed to assume an austenitic state at both ambient and body temperatures, but within the elastic or superelastic range of the material. Thus, the annular ring 118 may be elastically compressed into the contracted condition, but may resiliently expand towards the enlarged condition when released from any constraints maintaining the annular ring 118 in the contracted condition.

The annular ring 118 may be at least partially covered with fabric, e.g., for tissue ingrowth, by wrapping fabric around the annular ring 118, while accommodating expansion and contraction of the annular ring 118. Optionally, sutures and the like (not shown) may be used to secure the fabric to the annular ring 118, e.g., at locations removed from the ends, such as at an intermediate location about the circumference of the annular ring 118. Alternatively, the entire annular ring 118 may be free to slide within the fabric wrapped around the annular ring 118. Optionally, the gasket member 112 may also include a flexible skirt and/or baleen elements (not shown), e.g., surrounding the annular ring 118 and/or within the fabric covering the annular ring 118, which may bias a portion of the fabric covering outwardly.

With continued reference to FIG. 1, the sewing cuff 120 may be attached to or otherwise extend around the annular ring 118. The sewing cuff 120 may simply be one or more layers of fabric or other material covering at least a portion of the annular ring 118. For example, a layer of fabric (not shown) may cover all of the annular ring 118 (other than any connectors and/or bearing surfaces, if any) and/or may include a section of material extending radially outwardly from the annular ring 118.

Optionally, the sewing cuff 120 may include flexible core material (not shown) that may be attached to or otherwise extend around the annular ring 118. For example, the core may be secured around the annular ring 118 by an interference fit, bonding, fusing a portion of the core, and the like. The core may be substantially covered with fabric, similar to the annular ring 118.

In an exemplary embodiment, the core may include a lattice (not shown) extending around a circumference of the core, e.g., including at least two spaced apart circumferential elements and a plurality of ribs or transverse elements extending between the circumferential elements, thereby defining openings through the lattice. The openings may be completely open, i.e., free from any material. Alternatively, the openings may be recesses including a relatively thin wall of core material, i.e., that is substantially thinner than the circumferential elements and/or ribs. In other embodiments, the core may include a base or web and a plurality of fins or ribs extending from the web to provide a flexible structure that may facilitate sealing between the sewing cuff 120 and valve member 114.

Exemplary materials for the core include silicone or other elastomeric materials, foam, fabric, felt, polymers, and the like. In addition or alternatively, the core may include swellable material, e.g., foam or sponge materials that may expand when exposed to fluid, such as blood. The materials may be molded or otherwise formed into the core, e.g., using known molding, extrusion, cutting, or other manufacturing procedures. For example, the core may be injection molded or otherwise formed in its annular shape.

Alternatively, the core may be molded or otherwise formed as a flat sheet, and rolled into the annular shape. In this alternative, the ends of the sheet may be attached to one another, e.g., using sutures, adhesives, ultrasonic welding, and the like. Optionally, to provide a tapered shape, one or more wedges (not shown) may be cut out of the band to provide a desired tapered but annular shape. In another option, portions of the core may be disconnected from other portions, e.g., to prevent puckering. For example, if the core is formed from a rolled sheet (not shown), ends of the sheet (also not shown) may remain loose to allow the ends to move relative to one another.

In a relaxed state (free from external forces), the sewing cuff 120 may adopt an undulating annular shape or a generally planar annular shape. The sewing cuff 120 may also be tapered, as shown in FIG. 1, e.g., having a larger diameter or circumference about an upper edge than about an edge adjacent the annular ring 118. The tapered shape of the sewing cuff 120 may define an angle relative to the longitudinal axis 117, e.g., between about twenty and forty five degrees (20-45°).

The material of the core may be substantially flexible, e.g., manufactured in a desired annular shape, yet easily deformed, e.g., deflected, stretched, and/or compressed. The core may be sufficiently flexible to be "floppy," i.e., such that the core conforms easily to the particular anatomy and/or implantation arrangements encountered during implantation. Thus, when the sewing cuff 120 is placed above or within a biological annulus within a patient's heart, the core may conform to the surrounding anatomy and/or may deform when the valve member 114 is secured to the gasket member 112, e.g., to enhance sealing between the valve member 114 and the gasket member 112, as described further below.

Optionally, the gasket member 112 may include one or more additional components. For example, the gasket member 112 may include a collar or stand-off (not shown) that extends upwardly from the sewing cuff 120 for receiving the valve member 114. Additional information on materials, construction, and/or components of the gasket member 112 may be found in U.S. Publication Nos. US 2004/0122516, filed as Ser. No. 10/327,821, US 2005/0165479, filed as Ser. No. 10/765,725, US 2006/0195184, filed as Ser. No. 11/069,081, and US 2007/0016285, filed as Ser. No. 11/420,720, and in co-pending application Ser. No. 11/567,735, filed Dec. 6, 2006. The entire disclosures of these references are expressly incorporated by reference herein.

With additional reference to FIG. 2, the guide rails 150 may include elongate bands, fibers, or filaments including a first or distal end 153 attached or otherwise secured to the gasket member 112 and a second or proximal end 152. Optionally, the guide rails 150 may include one or more depth markers or other elements (not shown) spaced apart along at least a portion of their lengths, e.g., immediately adjacent the first end 153 and/or at one or more predetermined distances from the gasket member 112. In addition or alternatively, the guide rails 150 may include one or more retention elements 154, e.g., locking beads, latches, catches, ratcheting elements, and the like, for securing the valve member 114 to or adjacent the gasket member 112.

As shown in FIG. 2, the guide rails 150 may be flat bands, e.g., formed from plastic or other material, and may have the retention elements 154 formed therein or attached thereto, as described in application Ser. No. 11/567,735, incorporated by reference herein. Alternatively, the guide rails 150 may be formed from wire or suture materials, e.g., formed from plastic, such as polyethylene, metal, such as stainless steel, cat gut, or composite materials, using known methods. The guide rails 150 may have sufficient column strength to maintain a substantially straight and/or upward orientation, but may be sufficiently flexible to be movable, e.g., laterally towards or away from the central axis 117 of the gasket member 112.

The retention elements 154 may be integrally formed on the guide rails 150, e.g., at the time the guide rails 150 are formed or by removing some of the guide rail material, and/or may be separate elements (made from the same or different materials than the guide rails 150) that are bonded, fused, or otherwise attached to the guide rails 150 at predetermined locations. In alternative embodiments, the retention elements 154 on the guide rails 150 may include knots (not shown) tied onto the guide rails 150 and/or beads (also not shown) formed on the guide rails 150 at predetermined locations. Although only one retention element 154 is shown on each guide rail 150, multiple retention elements 154 may be provided spaced apart from one another along each guide rail 150, similar to the elements shown in US 2005/0165479, incorporated by reference herein.

With continued reference to FIG. 2, in one embodiment, the retention elements 154 may include tapered or ramped proximal edges 154a and substantially blunt distal edges 154b. The tapered proximal edges 154a may provide a transition allowing the valve member 114 to be passed distally over the retention elements 154. The blunt distal edges 154b may provide locks that prevent the valve member 114 from being passed proximally back over the retention elements 154, as described further below.

The distal end 153 of each guide rail 150 may be attached to the gasket member 112, e.g., using one or more sutures, adhesives, and the like. For example, each guide rail 150 may include one or more holes (not shown) through the distal end 153 that may receive one or more sutures. The sutures may be directed through the holes and driven through the fabric covering and/or a portion of the sewing cuff 120 to secure the distal end 153 to the gasket member 112. In addition or alternatively, the distal ends may be attached to the gasket member 112 using an adhesive, by receiving the distal end 153 through a portion of the gasket member 112, e.g., through the fabric covering or sewing cuff 120, and the like. Optionally, the distal end 153 may be fused to or embedded in a core of the sewing cuff 120.

The guide rails 150 may be spaced apart from one another about the circumference or periphery of the gasket member 112. For example, the guide rails 150 may be provided on portions of the gasket member 112 that are aligned with the commissures (not shown) on the valve member 114 and/or a biological annulus into which the gasket member 112 is to be implanted. Thus, for example, for a prosthesis for an aortic valve having three commissures, three guide rails 50 may be provided, as shown in FIGS. 1 and 2. However, if desired one, two, or more guide rails (not shown) may be provided on the gasket member 112.

With additional reference to FIGS. 3, 4A, and 4B, the guide shields 156 may extend upwardly and/or outwardly from the sewing cuff 120, e.g., to at least partially define a passage 124 therebetween for guiding the valve member 114 downwardly towards the gasket member 112, as shown in FIG. 1 and described further below. The guide shields 156 may be formed from a relatively thin and/or transparent sheet, e.g., a plastic such as polyester, Mylar®, or any other polymeric film or material, such as high-density or low-density polyethylene, polystyrene, and the like. The sheet may be cut or otherwise formed to into a desired shape, such as a "mandolin" or inverted "Y" shape, e.g., defining a relatively wide base 156a that may be attached to the gasket member 112 and a relatively narrow loose upper end 156b. Alternatively, the guide shields may have a generally triangular (not shown), e.g., optionally including a central open portion, thereby defining a pair of inverted "V" shaped bands (not shown) extending from the upper end 156b to the base 156a.

The guide shields 156 may be sufficiently rigid to maintain their shape and/or orientation, but may be sufficiently flexible to be deflected, folded, or bent, if desired, e.g., to facilitate access around the guide shields 156. The transparency of the film may be pretty useful for seeing through the guide shields 156, e.g., to locate the gasket member 112 relative to or within a biological annulus, relative to other anatomical structures, and the like, without having to move the guide shields 156 out of the way.

Optionally, the upper end 156b may include one or more openings 158 for receiving the guide rails 150 therethrough. The openings 158 may partially restrain the guide rails 150 away from the passage 124 or otherwise out of the operator's field of view during a procedure when the guide rails 150 are received in the openings 158, as described further below. Optionally, the upper ends 156b of the guide shields 156 may be split, e.g., including a slot 158a extending down to the openings 158 to facilitate inserting and/or removing the guide rails into/from the openings 158. Alternatively, as shown in FIG. 4D, the upper end 156b' of the guide shields 156' may include a slot 158a' that extends to or enters the opening 158' from the side or below and extends to a side edge of the upper ends 156b'. Such a slot 158a' may provide side access to the opening 158', yet still provide an opening 158' that may securely capture a guide rail 150 (not shown in FIG. 4D).

In addition or alternatively, the guide shields 156 and/or guide rails 150 may include one or more other detents, connectors, and the like for releasably constraining the guide rails 150 relative to the guide shields 150. For example, as shown in FIG. 3, the upper end 156b of the guide shield 156 may include a seatbelt or "zip tie" arrangement 159 for releasably constraining a guide rail adjacent the guide shield 156. The arrangement 159 may include an elongate belt or tab 159a extending laterally from the upper end 156b of the guide shield 156, and a slot or other receptacle 159b opposite the tab 159a. Optionally, the tab 159a may include one or more connectors 159c, e.g., ratchets, detents, or other retention elements, that may secure the tab 159a at one or more positions within the receptacle 159b. In addition or alternatively, the arrangement 159 may facilitate imparting a desired shape to the guide shield 156, e.g., by constraining the guide shield 156 in a curved shape around the longitudinal axis 117 when the tab 159a is securely received in the receptacle 159b, e.g., to provide better access and/or visualization to the gasket member 112 during implantation.

Figure 3:
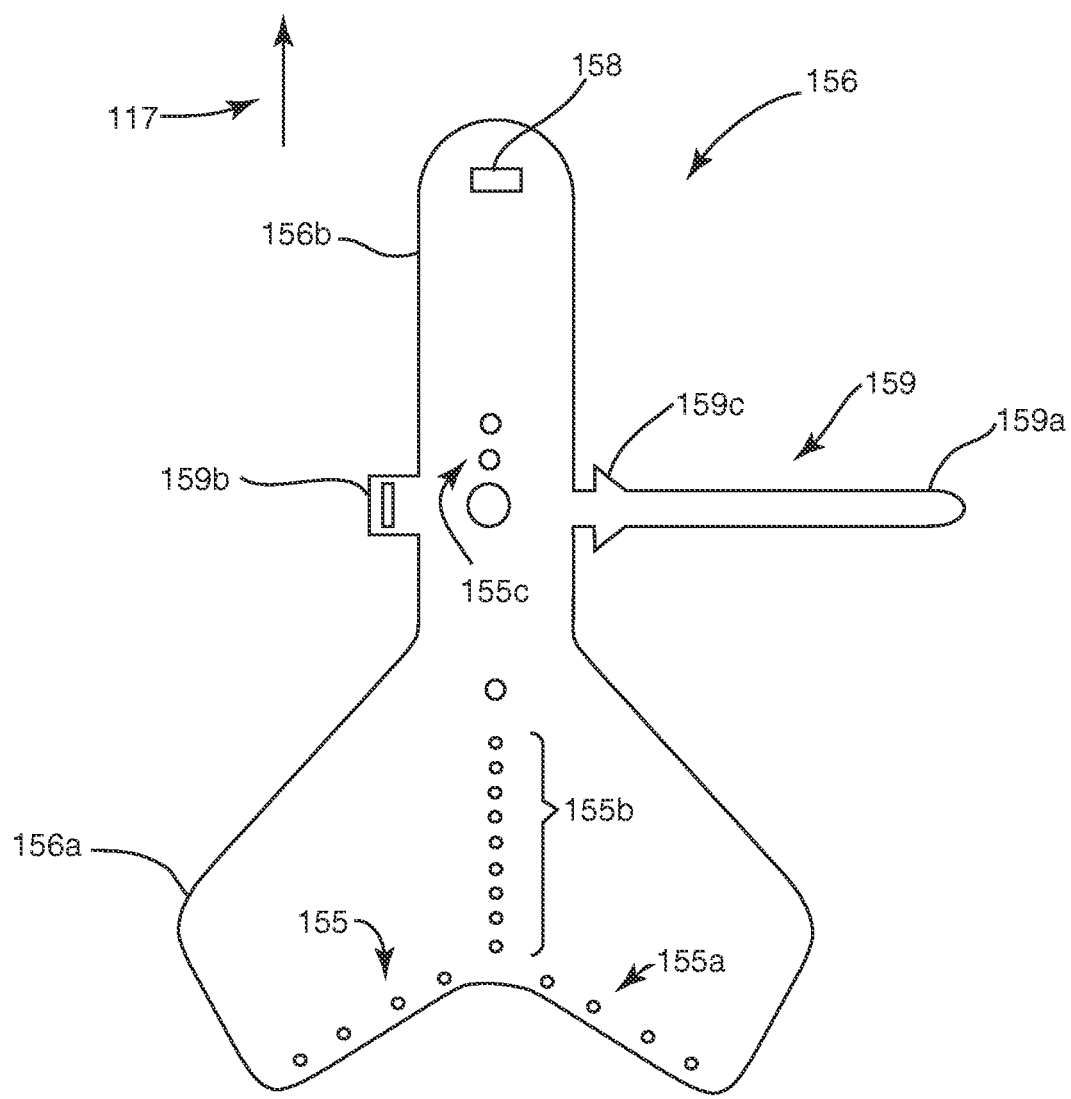
FIG. 3 is a front view of an exemplary embodiment of a guide shield that includes suture holes, a receiving slot for a guide rail, and a belt and buckle.
Figure 4A:
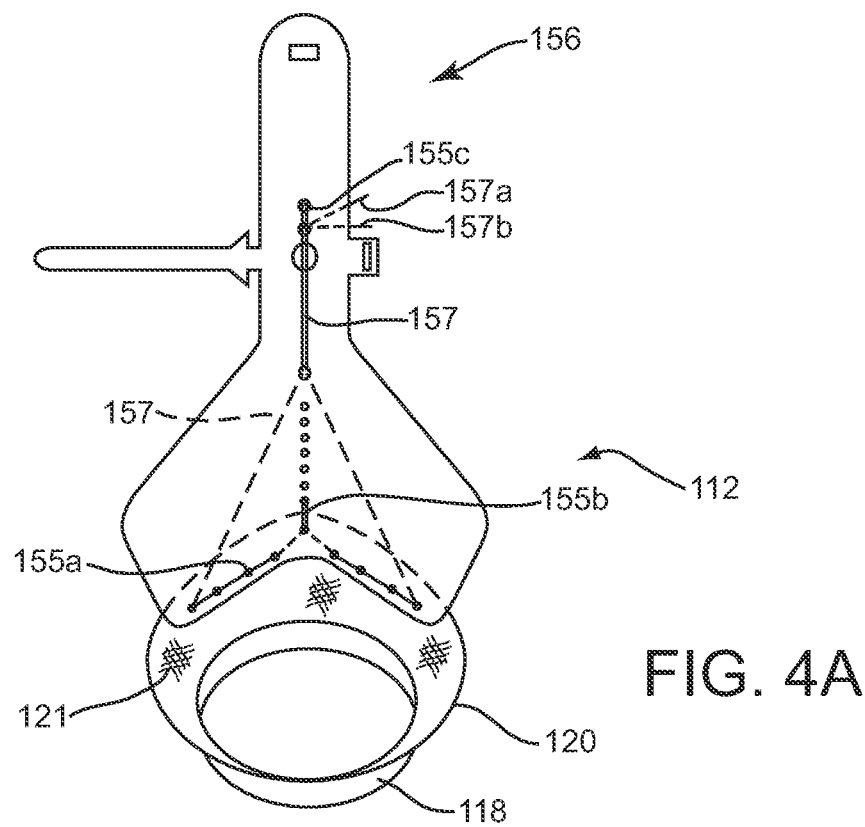
FIGS. 4A and 4B are top and side views, respectively, of a guide shield being attached to a gasket member with sutures.
Figure 4B:
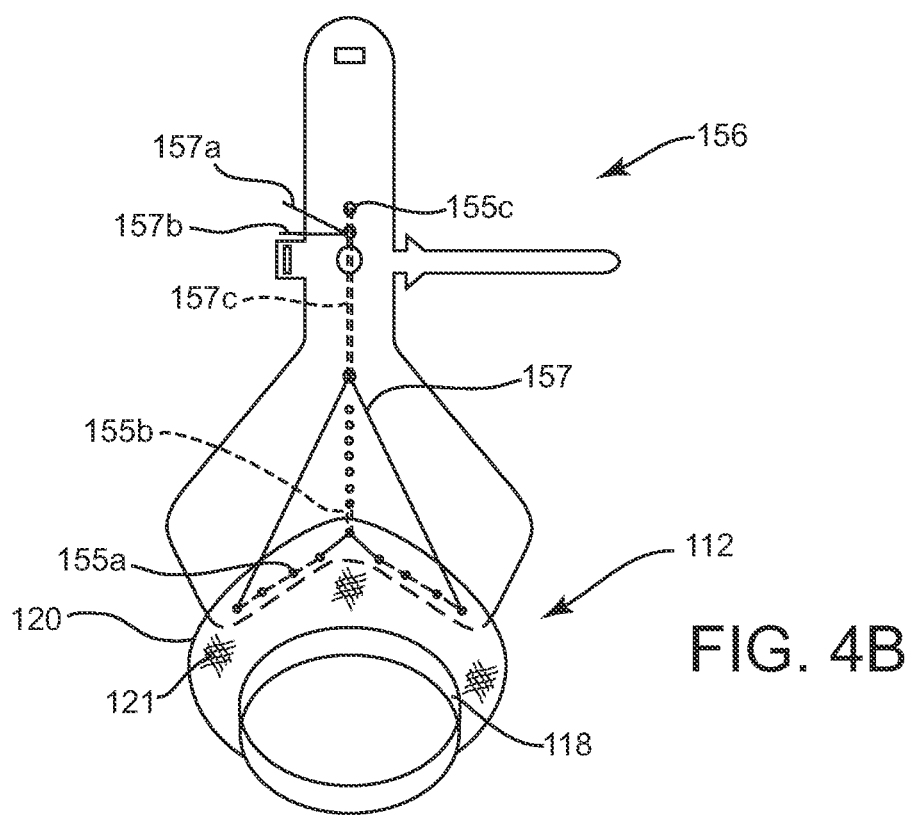

With continued reference to FIGS. 3, 4A, and 4B, each guide shield 156 may include a plurality of holes for facilitating removably attaching the guide shield 156 to the gasket member 112. For example, as best seen in FIG. 3, a plurality of holes 155a may be disposed along the base 156a of each guide shield 156 for receiving sutures or other fastening elements, which may be driven into the fabric covering 121, sewing cuff 120, and/or other portion of the gasket member 112, as best seen in FIG. 4A. In addition, the guide shield 156 may include a plurality of holes 155b, 155c extending and/or spaced apart generally axially along the guide shield 156, e.g., a vertical array of holes 155b along the base 156a and a set of holes 155c along the upper end 156b.

In addition, the vertical array of holes 155b along the base of 156a may provide preferential flexibility along an axis defined by the holes 155b, e.g., to act as a hinge or to provide a preferred bending edge for shaping the guide shield 156, for example, during folding process. For example, before attaching the guide shields 156 to the gasket member 112, the guide shields 156 may be bent vertically, e.g., along the axis of the holes 155b, to shape the guide shields 156 similar to the commissures of the sewing cuff 120. The bends may reduce the force required to deform the guide shields 156 during bending and/or to provide a more compact folded shape when the gasket member 112 is loaded onto a gasket delivery tool, such as that described elsewhere herein. In addition, the bend may bias the guide shield 156 towards a desired shape, e.g., when the gasket member 112 has been released or otherwise placed within a biological annulus or other implantation site.

Turning to FIGS. 4A and 4B, an exemplary method is shown for attaching a guide shield 156 to a gasket member 112. A suture 157 including a first end 157a and a second end 157b may be routed through the holes 155 to removably secure the guide shield 156 relative to the gasket member 112. For example, the first end 157a may be routed through one or more holes 155c in the upper end 156b, through one or more holes in the intermediate array of holes 155b, and into a hole 155a on one end of the base 156a. The suture 157a may then be directed through the holes 155a along the base 156a and through the fabric covering 121 of the gasket member 112, e.g., from the one end of the base 156a to the opposite end thereof. The suture 157 may then be routed back through one or more of the array of holes 155b and the set of holes 155c, and then the first end 157a may be tied or otherwise secured to the second end 157b, e.g., by knot 157c.

Figure 4C:
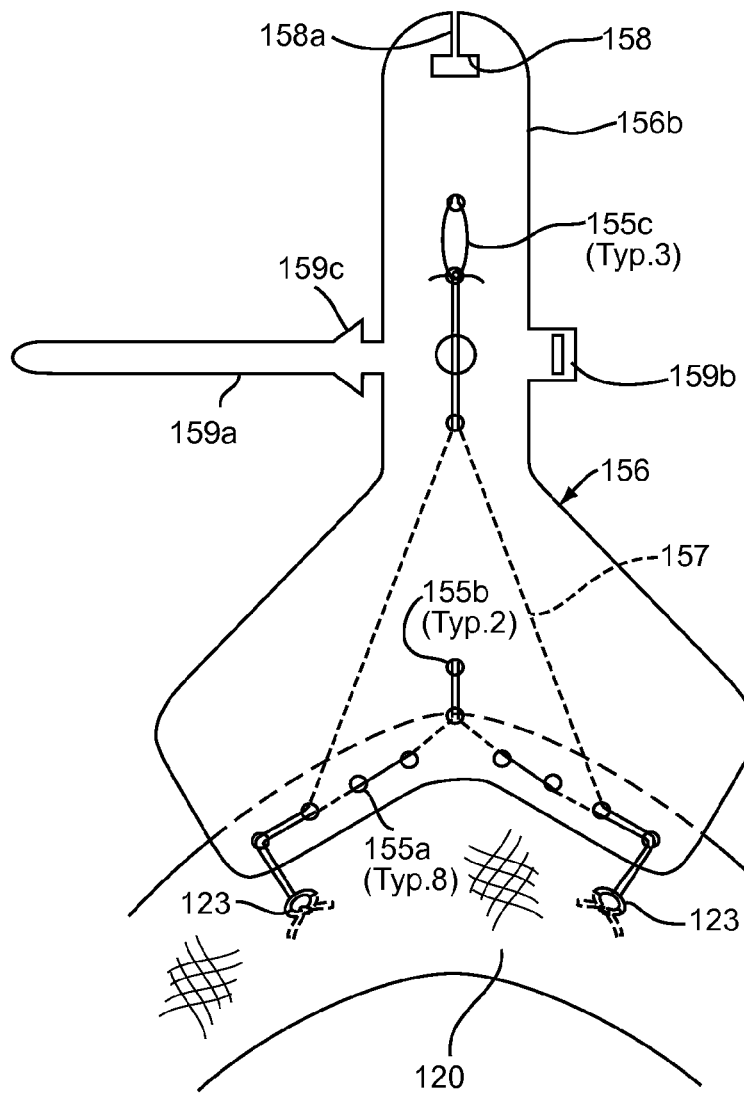
FIG. 4C is a detail of an alternative method for releasably securing the guide shield of FIGS. 4A and 4B to anchor loops on a gasket member.
Figure 4D:
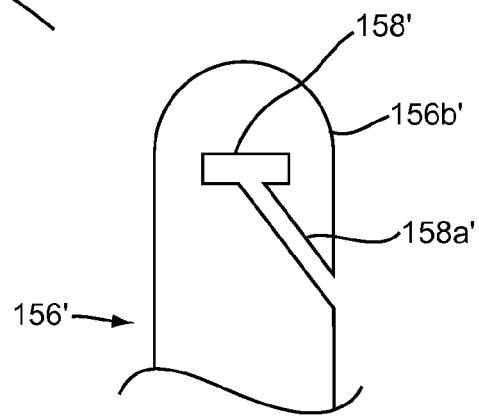
FIG. 4D is a detail of an alternative embodiment of an upper end of a guide shield.

Optionally, as shown in FIG. 4C, the sewing cuff 120 of the gasket member 112 may include one or more anchoring loops 123, e.g., sewn into or otherwise secured to the sewing cuff 120, fabric covering 121, or otherwise to the gasket member 112. The loops 123 may facilitate passing sutures therethrough, e.g., when releasing the guide shields 156 from the gasket member 112. As shown, the loops 123 are shown at locations corresponding to holes 155a adjacent the opposite ends or wings of the base 156a.

An exemplary method for attaching the guide shield 156 to the gasket member 112 may include initially providing a set of guide shields 156, e.g., three, made using the procedures and/or materials described elsewhere herein. Before sewing the guide shields 156 to the gasket member 112, the guide shields 156 may be cleaned and/or sterilized, e.g., by ultrasonic cleaning and/or rinsing with purified water. The guide shields 156 may be folded vertically, e.g., along the vertical holes 155b and/or to bend the upper end 156b outwardly. The guide shields 156 may then be sutured to the gasket member 112, e.g., by initially putting a suture anchor loop on the surface of the gasket member 112, e.g., using a needle pair on ends of a length of suture, e.g., at the center of the base 156a. The sutures may then be stitched outwardly towards the ends of the base 156a, e.g., through the anchor loops 123, and then up to the upper holes 155c, where the suture ends may be tied, as shown in FIG. 4C.

In this configuration, the guide shield 156 may be removed from the gasket member 112 simply by cutting or otherwise severing the suture 157. Optionally, a chain stitch or other stitch may be used, e.g., that may be loosened upon being cut at a single location, which may facilitate removing the sutures and, consequently, the guide shields 156 after implantation. Optionally, one of the ends 157a, 157b of the suture 157 may be looped and/or secured through the holes 155c in the upper end 156b, e.g., to prevent the suture 157 from separating entirely from the shield guard 156. For example, one side of the suture 157 may be cut below the location where the end(s) 157a, 157 are secured, and the suture may then be pulled from the other side, e.g., to cause the cut side to travel through the various holes 155. Thus, even the suture 157 may be separated entirely from the gasket member 112, thereby allowing the guide shield 156 to be removed from the gasket member 112. Thus, the suture 157 may be removed with the guide shield 156, thereby avoiding the risk of leaving the suture 157 or a portion thereof behind. In addition, this configuration may allow the suture 157 to be cut and the guide shield 156 removed simply by introducing a cutting tool (not shown) to the upper end 156b of the guide shield 156, rather than requiring the cutting tool to be introduced all the way to the base 156a of the guide shield 156.

In addition or alternatively, the suture 157 may be formed from slippery material, e.g., Gore-Tex® expanded polytetrafluoroethylene (ePTFE), polyester, ultra-high molecular weight polyethylene (UHMWPE), polyethylene, and the like, which may slide easily out of the various holes 155 when pulled from one end. Alternatively, if additional security is required, the suture 157 may be knotted or otherwise secured at one or more locations along or between the various holes 155, although this may require cutting or otherwise severing the suture 157 at multiple locations before the guide shield 156 may be removed from the gasket member 112. In this alternative, one or more sutures 157 may be secured through the holes 155a in the base 156a and the fabric covering 121 (or other component of the gasket member 112). For example, individual sutures (not shown) could be introduced through respective holes and portions of the gasket member 112. In a further alternative, the holes 155 may be deleted and the suture 157 may simply be directed through desired locations of the guide shield 156, e.g., using a sharp needle or other instrument carrying the suture 157.

Referring back to FIG. 1, the valve member 114 generally includes an annular shaped body or frame 132 and one or more leaflets or other valve elements 133. The valve member 114 may include a fabric covering 135, similar to the gasket member 112, e.g., covering the frame 132 and/or other components of the valve member 114, other than the leaflets 133.

The frame 132 may have a noncircular, e.g., a multiple lobular shape corresponding to a shape of the biological annulus within which the valve member 114 is to be implanted. For example, the valve member 114 may have a tri-lobular shape, including three lobes separated by cusps or scallops 134, e.g., corresponding to a sinus of Valsalva above an aortic valve site. In one embodiment, the valve member 114 may be a bioprosthetic valve member, e.g., an annular frame 132 carrying a plurality of tissue leaflets 133. The frame 132 may include a plurality of struts (also not shown for clarity) that may be attached to and/or otherwise carry the leaflets 133. For example, the struts may include a laminate structure, including two or more sheets of flexible material, similar to the valves disclosed in U.S. Pat. No. 6,371,983, and U.S. Publication No. US 2006/0276888, filed as Ser. No. 11/144,254, the entire disclosures of which are expressly incorporated by reference herein.

Alternatively, the valve member 114 may be a connecting device to which a valve (not shown) may be connected or that may otherwise receive a valve component, such as the connection adapter elements shown in U.S. Publication No. US 2005/0043760, filed as 10/646,639, the entire disclosure of which is expressly incorporated by reference herein. In another alternative, the valve 114 may include a mechanical valve or other valve (not shown), such as those disclosed in US 2005/0165479 and US 2007/0016285, incorporated by reference herein.

Optionally, the valve member 114 may include one or more introducers or receivers (not shown) through which the guide rails 150 may be received. For example, the receivers may include receptacles attached to desired locations on the valve member 114, e.g., to the fabric covering 135 at the commissures or other desired locations around the periphery of the frame 132. The receptacles may include one or more connectors (not shown) that interact with connectors on the guide rails 150, such as retention elements 154. Alternatively, the valve member 114 may simply include slots, e.g., through the fabric covering 135 and/or frame 132, through which the guide rails 150 may be slidably received. In this alternative, the valve member 114 and/or gasket member 112 may include one or more connectors (not shown) for securing the valve member 114 to or adjacent to the gasket member 112. For example, the gasket member 112 may include a collar (not shown) extending upwardly from the sewing cuff 120 and/or annular ring 118, and the valve member 114 may be received in the collar. Additional information on apparatus and methods for securing the valve member 114 relative to the gasket member 112 may be found in the references incorporated by reference above or in U.S. Publication No. US 2006/0235508, filed as 11/279,246, or U.S. application Ser. No. 11/668,459, filed Jan. 29, 2007, the entire disclosures of which are expressly incorporated by reference herein.

Figure 5A:
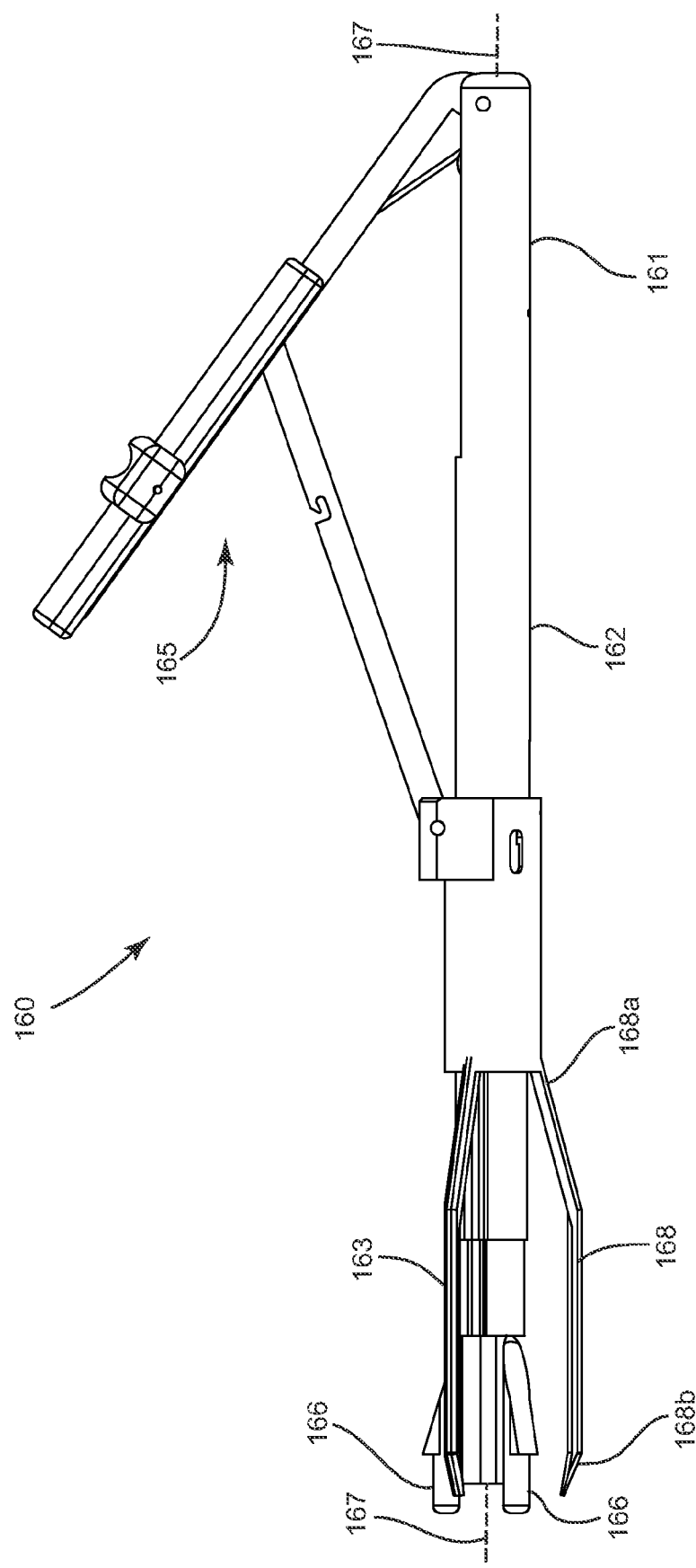
FIGS. 5A-5C are side, perspective, and end views, respectively, of a tool for delivering the gasket member of FIG. 2.
Figure 5B:
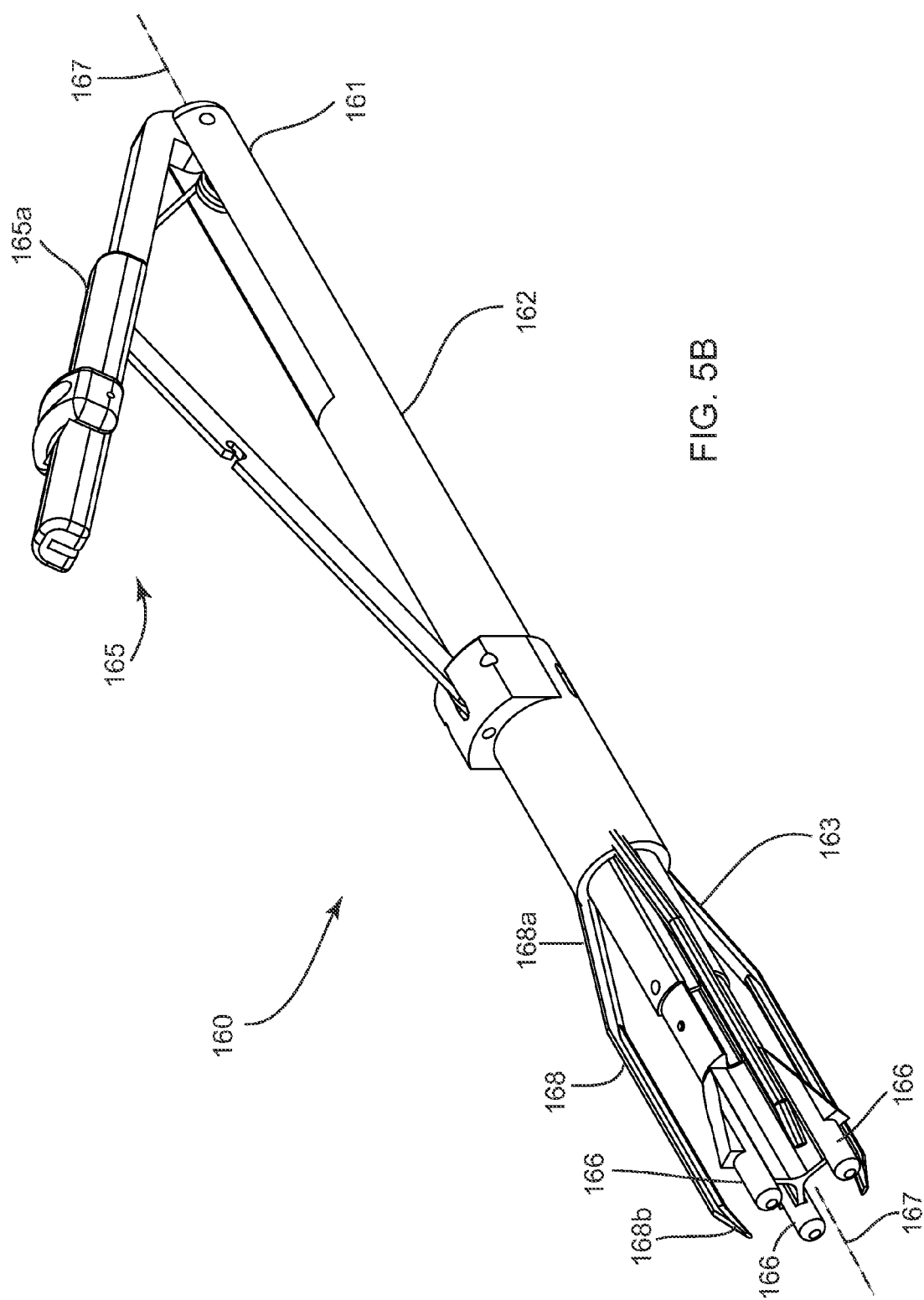
Figure 5C:
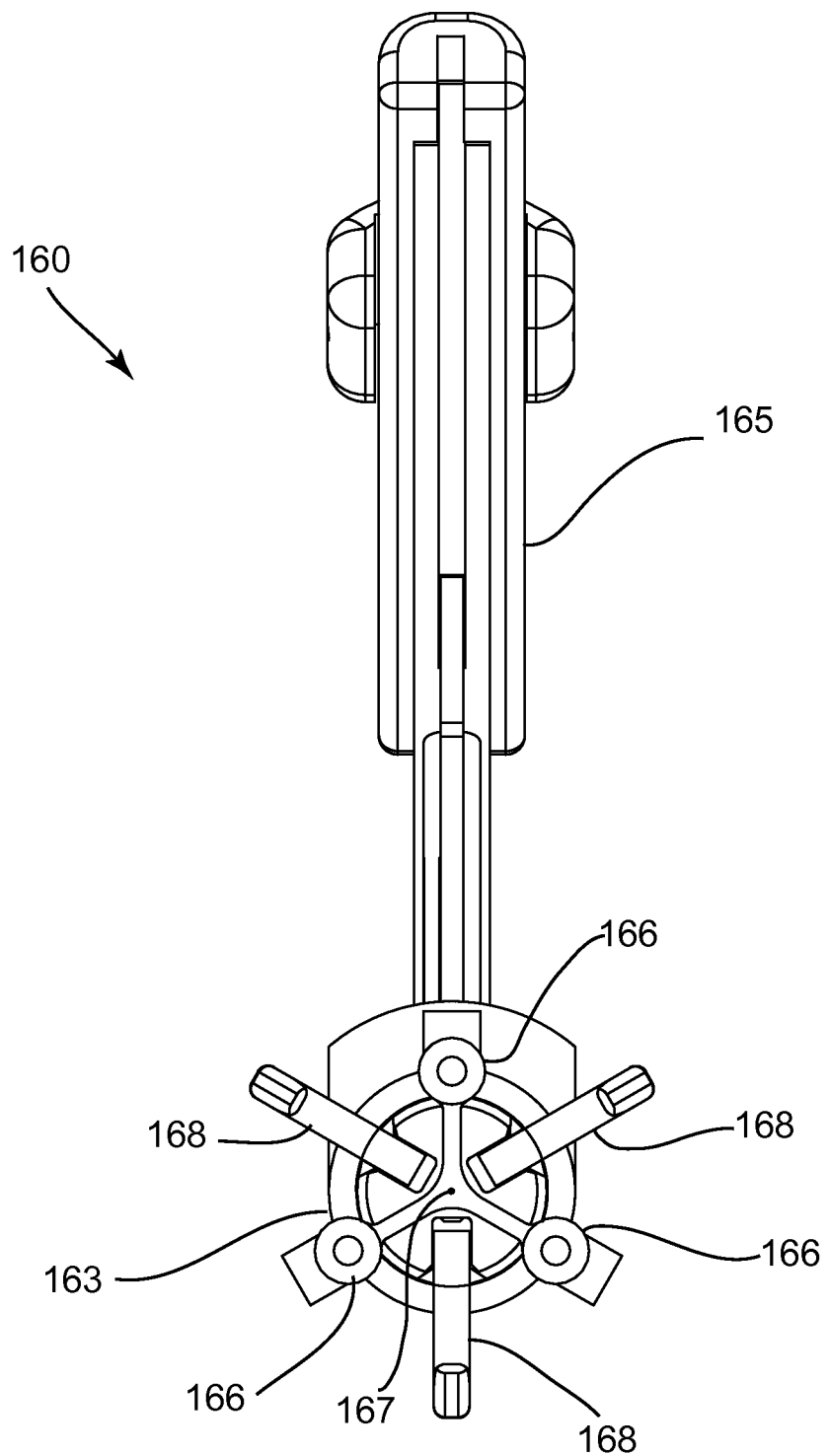

Turning to FIGS. 5A-5C, an exemplary embodiment of a gasket delivery tool 160 is shown that generally includes a shaft 162 including a proximal end 161, a distal end 163, and an actuator 165 on the proximal end 161. With additional reference to FIGS. 6A and 6B, the delivery tool 160 may include a plurality of supports 166 on the distal end, e.g., spaced apart around a longitudinal axis 167 of the tool 160. The supports 166 may be substantially rigid cylindrical hubs for receiving a gasket member 112 (such as any of those described herein) around the supports 166. The supports 166 may generally define a diameter that is smaller than the gasket member 112, e.g., smaller than the radius of the annular ring 118.

In addition, the tool 160 may include a plurality of arms 168 movably mounted to the distal end 163. For example, one end of the arms 168 may be fixedly attached to the distal end 163 of the tool 160, e.g., proximal to the supports 166, and the other end may include tips disposed adjacent the supports 166. As shown, the arms 168 may be offset radially relative to the supports 166 such that each arm 168 is disposed between adjacent supports 166. The arms 168 may be movable from an outer position (not shown), defining a radius larger than the gasket member 112 to an inner position (shown in FIGS. 6A and 6B), wherein the tips are disposed between and/or within the supports 166.

Figure 6A:
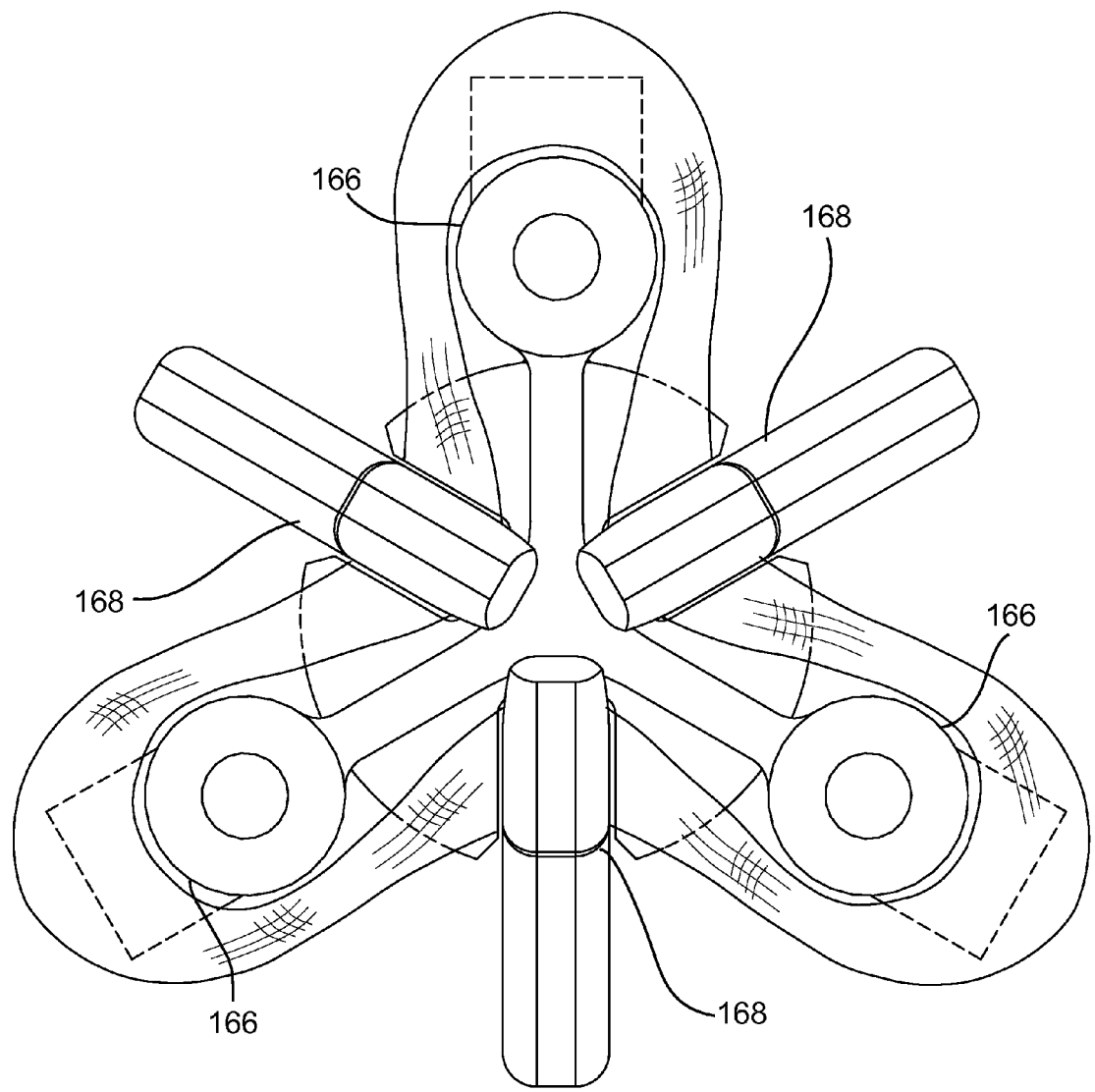

The actuator 165 may include a lever or other mechanism that may selectively move the tips of the arms 168 between the outer and inner positions. During use, with the arms 168 in the outer position, a gasket member 112 may be placed between the supports 166 and the arms 168, e.g., with the nadir regions of the sewing cuff 120 aligned radially with the arms 168. The arms 168 may then be directed to the inner position, thereby securing the gasket member 112 between the supports 166 and the arms 168. As shown in FIGS. 6A and 6B, the gasket member 112 may be deformed from a generally circular expanded condition to a multiple lobed, e.g., "shamrock" shaped contracted condition defining lobes. The gasket member 112 may be elastically deformed into the contracted condition or plastically deformed, e.g., in a martensitic state, similar to the previous embodiments.

Figure 7C:
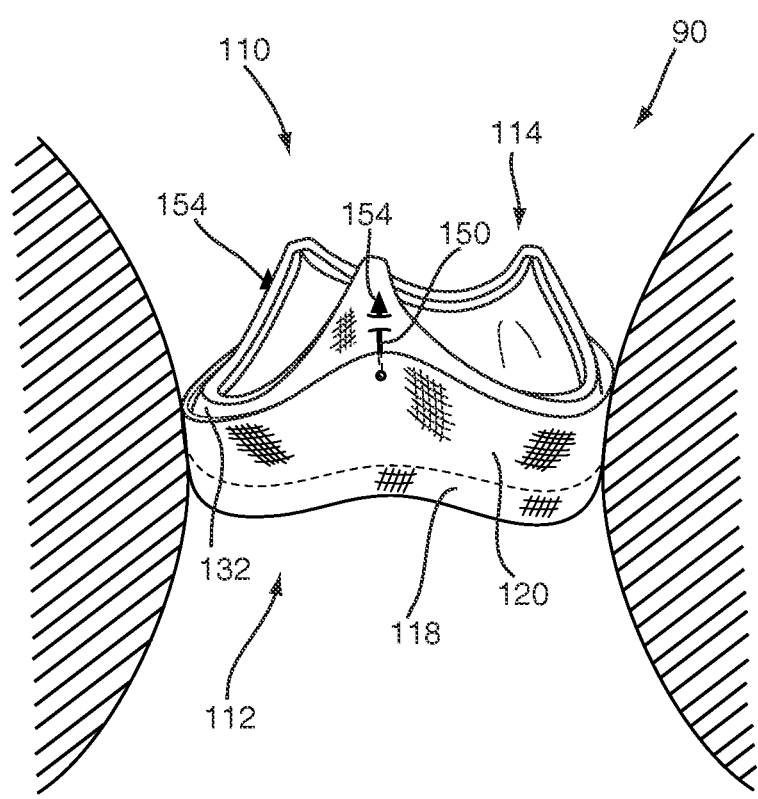

Turning to FIGS. 7A-7C, during use, the heart valve assembly 110, which may include any of the embodiments described herein, may be implanted within a patient's body, e.g., within or adjacent to a biological annulus 90. The biological annulus 90 may be the site for replacing an existing natural or previously implanted heart valve, such as a tricuspid, mitral, aortic, or pulmonary valve within a patient's heart (not shown).

Before implanting the heart valve assembly 110, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve and/or leaflets (also not shown) may then be removed from the annulus 90 using known methods.

A heart valve assembly 110, including a gasket member 112 and a valve member 114 may be selected based upon the anatomy encountered, e.g., having a plurality of lobes, matching the lobes of the biological annulus 90 and/or having a cross-sectional dimension corresponding to the interior cross-section of the biological annulus 90. Optionally, a gasket member 112 and/or valve member 114 may be selected having a size that is larger than the biological annulus 90. For example, the gasket member 112 may have a diameter in its relaxed condition that is slightly larger than the biological annulus 90, e.g., such that the gasket member 112 may at least partially dilate the biological annulus 90 upon implantation. In addition or alternatively, the valve member 114 may have a diameter or other cross-section that is substantially larger than the biological annulus 90, e.g., for supra-annular or intra-sinus implantation, which may accommodate the larger size.

As shown in FIGS. 6A and 6B, the gasket member 112 may be loaded onto the tool 160, e.g., in the contracted condition as described above. The gasket member 112 may be loaded onto the tool 160 immediately before introduction, or may be prepared in advance, as desired.

Turning to FIG. 7A, the gasket member 112 and distal end 163 of the tool 160 may then be directed into the biological annulus 90 in the direction of arrow 94. The tool 160 may be rotated about its longitudinal axis, if necessary, to align the lobes of the gasket member 112 with the commissures (not shown) of the biological annulus 90. As shown in FIG. 7B, the gasket member 112 may be positioned such that the annular ring 118 is received within the valve annulus, e.g., from which the native leaflets (or prosthesis) has been removed, and the sewing cuff 120 is disposed supra-annularly, e.g., within the Sinus of Valsalva.

The arms 168 may then be directed to the outer position, e.g., using the actuator 165 on the tool 160, thereby releasing the gasket member 112 within the biological annulus, as shown in FIG. 7B. As shown, the gasket member 112 may resiliently expand towards its original expanded condition when released, e.g., to dilate the biological annulus 90 or otherwise direct the surrounding tissue 98 outwardly. The tool 160 may be removed, leaving the gasket member 112 in place within the biological annulus 90. As shown, the annular ring of the gasket member 112 may be located within a native valve annulus, while the sewing cuff 120 is located in a supra-annular position relative to the native valve annulus. In an alternative embodiment, a dilation tool (not shown) may be advanced into the gasket member 112 and expanded to forcibly (e.g., plastically) expand the annular ring 118 within the biological annulus 90.

Also as shown in FIG. 7B, the guide shields 156 and guide rails 150 may extend upwardly and/or outwardly from the gasket member 112. The guide shields 156 may be sufficiently long such that upper ends of the guide shields 156 are disposed outside the patient's body and/or outside the biological annulus. For example, the guide shields 156 may extend through an incision or other relatively narrow passage above the biological annulus 90. The guide shields 156 may at least partially define a passage 124 communicating through the biological annulus 90, the inner surfaces of the guide shields 156 providing a smooth and/or lubricious surface to facilitate advancing the valve member 114 into the tissues annulus 90 towards the gasket member 112.

After releasing the gasket member 112 in the biological annulus 90, the gasket member 112 may be secured to the surrounding tissue 98. For example, a tool (not shown) may be used to deliver a plurality of fasteners 96 through the sewing cuff 120 and into the surrounding tissue 98. Forceps, tweezers, or other tools may be used, if desired, to manipulate components of the gasket member 112 during delivery of the fasteners 96. For example, the tool (not shown) may be used to hold the sewing cuff 120 and/or to move the guide rails 150 and/or guide shields 156 out of the way. Because of the orientation, configuration, and/or transparency of the guide shields 156, the guide shields 156 may not obscure observation and/or access into the biological annulus to deliver the fasteners 96. Exemplary fasteners and methods for using them to secure the gasket member 112 may be found in U.S. Publication Nos. US 2004/0122516, filed as Ser. No. 10/327, 821, US 2005/0043760, filed as Ser. No. 10/646,639, US 2005/0080454, filed as Ser. No. 10/681,700, and US 2006/0122634, filed as Ser. No. 11/004,445, the entire disclosures of which are incorporated by reference herein.

Still referring to FIG. 7B, the desired valve member 114 may be preloaded onto a valve holder tool (not shown) by the manufacturer or the user, or a desired size valve (if multiple sizes are available) may be selected and loaded onto the valve holder, e.g., using one or more sutures. For example, a valve sizer (or a series of progressively larger valve sizers) may be directed into the biological annulus 90 to determine the appropriate size prosthetic valve to be delivered into the biological annulus 90.

As can be seen in FIG. 7B, guide rails 150 and guide shields 156 may extend out of the biological annulus 90 and/or otherwise from the gasket member 112. Each guide rail 150 may be loaded through a receiver 130 on the valve member 114, such as those described elsewhere herein, until the guide rail 150 exits an upper end of the receiver 130. Optionally, the guide rails 150 may be inserted into receptacles (not shown) in the valve holder, e.g., before or after being loaded through the receivers 130 on the valve member 114.

The valve holder, carrying the valve member 114 may then be directed into the biological annulus 90, e.g., over the guide rails 150. If the guide rails 150 are coupled to and/or constrained by the guide shields 156, the guide rails may be released from the guide shields 156 to allow the valve member 114 to slide freely down the guide rails 150 towards the gasket member 112. During introduction, the valve member 114 may slidably contact inner surfaces of the guide shields 156 extending from the gasket member 112. Thus, the guide shields 156 may provide a substantially smooth and/or lubricious surface, which may facilitate advancing the valve member 114 through a narrow and/or partially obstructed passage into the biological annulus 90. Optionally, at least the inner surfaces of the guide shields 156 may be coated with a lubricious coating and the like to minimize friction between the guide shields 156 and the valve member 114.

Optionally, the guide rails 150 may include one or more markers 151 at predetermined locations, e.g., known distances from the gasket member 112. The markers 151 may provide the user confirmation of the location of the valve member 114 relative to the gasket member 112, and/or may provide visual confirmation when the valve member 114 has been secured to the gasket member 112, e.g., by indicating that the valve member 114 has passed over retention elements 154 on the guide rails 150, has been received in a collar (not shown) on the gasket member 112, and/or otherwise has been connected to the gasket member 112. As described elsewhere herein, the valve member 114 may be advanced to engage the connectors on the valve member 112 with retention elements 154 and the like on the gasket member 112. To facilitate this, the user may pull or otherwise subject the guide rails 150 to proximal tension, while advancing the valve holder and/or valve member 114, e.g., until a "click" or other audible and/or tactile feedback is provided that confirms that the cooperating connectors are engaged. Each set of connectors may be engaged sequentially or simultaneously.

Optionally, the guide rails 150 may include a weakened region, e.g., above the retention elements 154 or may be otherwise severable above the retention elements 154. The guide rails 150 may then be severed or otherwise separated from the gasket member 112, e.g., above the retention elements 154, and the guide rails 150 removed from the patient's body. Alternatively, an actuator (not shown) of the valve holder (also not shown) may be pulled proximally or otherwise manipulated to break or otherwise sever the guide rails 150 at their respective weakened regions.

Referring to FIG. 7C, the guide shields 156 may be removed from the gasket member 112 before or after severing the guide rails 150. As described above with reference to FIGS. 4A and 4B, the sutures 157 may be cut or otherwise severed to release the guide shields 156 and allow their separation from the gasket member 112. Upon being severed, the sutures 157 may simply unravel, allowing the guide shields 156 and sutures 157 to be removed simultaneously from the gasket member 112. Alternatively, the guide shields 156 and sutures 157 may be removed separately from the gasket member 112 and from the patient's body. The valve member 114 may be released from the valve holder, e.g., before or after severing the guide rails 150 and/or removing the guide shields 156, thereby providing the heart valve assembly 110 implanted within the biological annulus 90.

Figure 8A:
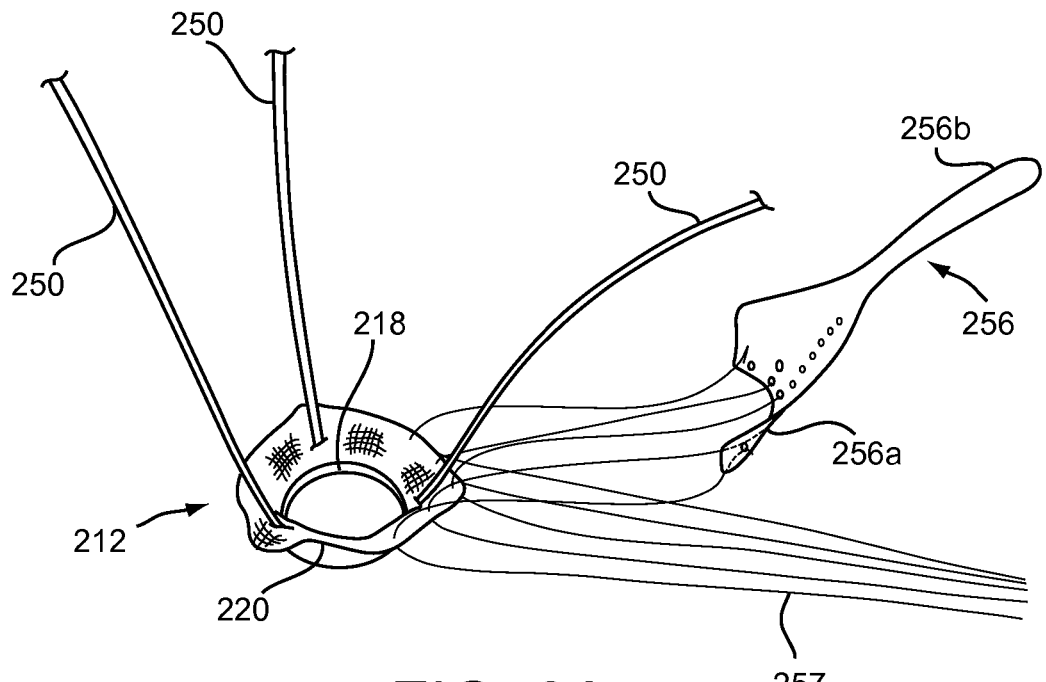
FIGS. 8A and 8B are perspective views of a gasket member including a guide shield slidable towards and away from the gasket member.
Figure 8B:
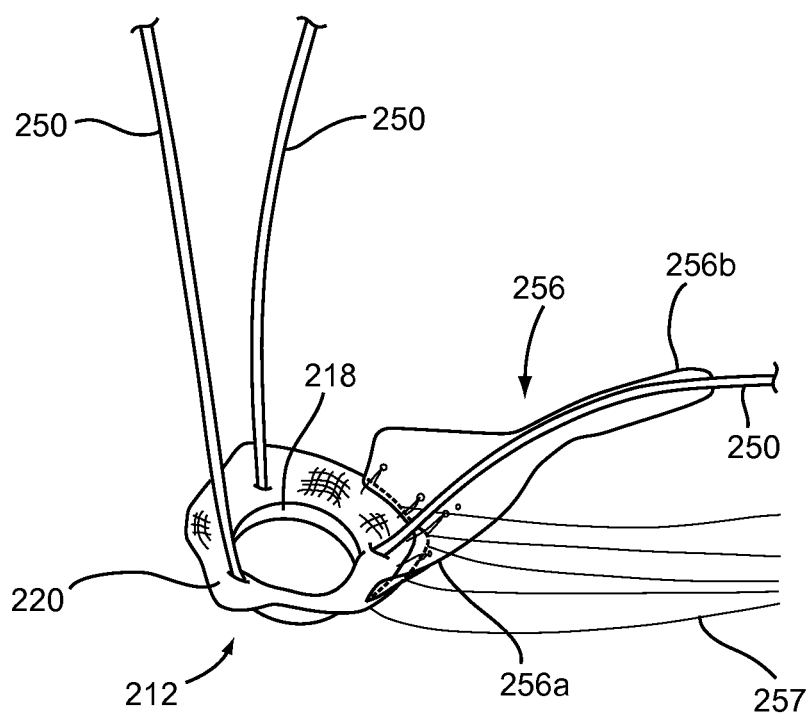

Turning to FIGS. 8A and 8B, another embodiment of a gasket member 212 is shown that includes a set of guide shields 256 (one shown for simplicity). The gasket member 212 may be formed similar to other embodiments described herein, e.g., including an annular ring 218, sewing cuff 220, and a plurality of guide rails or other leaders 250. Each of the gasket shields 256 may be formed generally similar to other embodiments described herein, e.g., including a broad base 256a and upper end 256b, which may include one or more features (not shown) for releasably constraining the guide rails 250 to respective guide shields 256.

Unlike other embodiments, each gasket shield 256 may include one or more sutures or other filaments 257 secured to the base 256a, which may be slidably received through a portion of the gasket member 212, e.g., through the sewing cuff 220 and/or fabric covering. Optionally, the sutures 257 may be received through loops (not shown) formed in the sewing cuff 220, if desired. The suture(s) 257 may be sufficiently long to extend completely out of a patient's body when the gasket member 212 is introduced into a biological annulus (not shown). The free ends of the sutures 257 may be braided or otherwise connected to one another such that the sutures 257 are pulled together.

Initially, as shown in FIG. 8A, the guide shields 256 may be provided away from the gasket member 212, but with the sutures 257 slidably received through the gasket member 212. The gasket member 212 may then be introduced into a biological annulus and implanted or otherwise secured therein, similar to other embodiments described elsewhere herein. The sutures 257 may be sufficiently long that the guide shields 256 may be disposed outside the patient's body, e.g., maintained out of the operating field. With the guide shields 256 away from the gasket member 212, the gasket member 212 may be more easily manipulated and/or monitored during introduction and implantation. For example, one or more clips, sutures, or other fasteners (not shown) may be delivered through the sewing cuff 220 into surrounding tissue without having to manipulate the guide shields out of the way.

Turning to FIG. 8B, once the gasket member 212 is secured within the biological annulus, the guide shields 256 may then be directed into biological annulus, e.g., by pulling the ends of the sutures 257. This action may cause the sutures 257 to slide through the gasket member 212, pulling the guide shields 256 into the biological annulus and against the sewing cuff 220, as shown, or otherwise adjacent the gasket member 212. A valve (not shown) may then be introduced into the biological annulus and secured to the gasket member 212, similar to other embodiments described elsewhere herein. When it is desired to remove the guide shields 256, e.g., after securing the valve to the gasket member 212, the upper ends 256b of the guide shields may simply be pulled, thereby causing the sutures 257 to slide through and out of the gasket member 212.

Alternatively, the guide shields 256 may be provided adjacent the gasket member 212, as shown in FIG. 8B, before the gasket member 212 is introduced into the biological annulus. For example, the gasket member 212 may be carried on a delivery tool (not shown), e.g., in a contracted condition, which may constrain the guide shields 256 with the gasket member 212. This may facilitate introduction of the gasket member 212 without dealing with the guide shields 256 being loose or otherwise separate from the gasket member 212, which may also require manipulating the sutures 257 to keep them out of the way.

Once the gasket member 212 is introduced into the biological annulus, the guide shields 256 may be pulled out of the biological annulus, i.e., to the position shown in FIG. 8A, before delivering fasteners through the gasket member 212, if desired. After delivering the fasteners, the guide shields 256 may be pulled into the biological annulus, as described above.

In another alternative, the guide shields 256 may remain adjacent the gasket member 212 while fasteners are delivered, similar to the previous embodiments. After introducing and/or securing a valve to the gasket member 212, the guide shields 256 may be removed, similar to the previous embodiments.

Figure 9A:
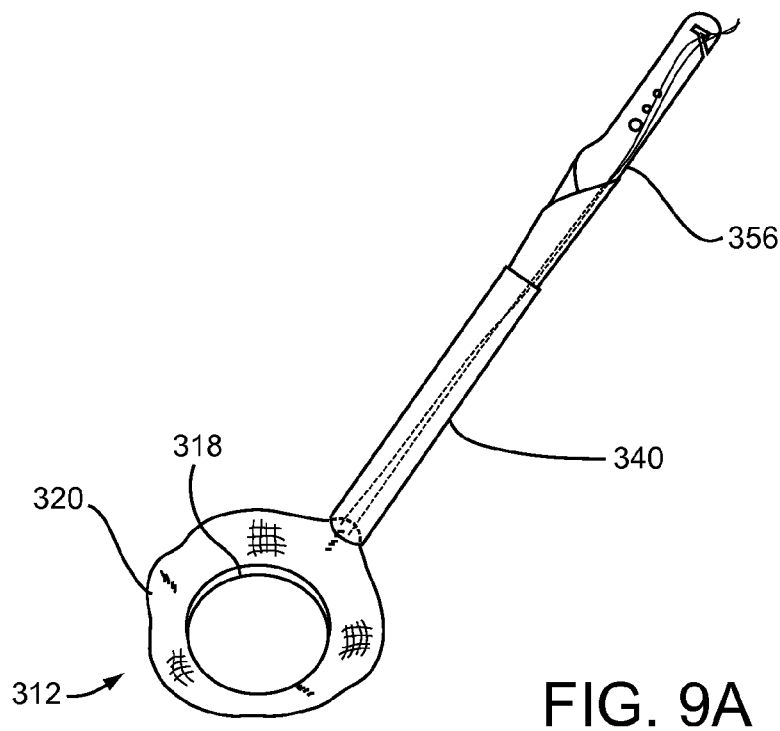
FIGS. 9A and 9B are perspective views of a gasket member including a guide shield constrained within a removable sleeve.
Figure 9B:
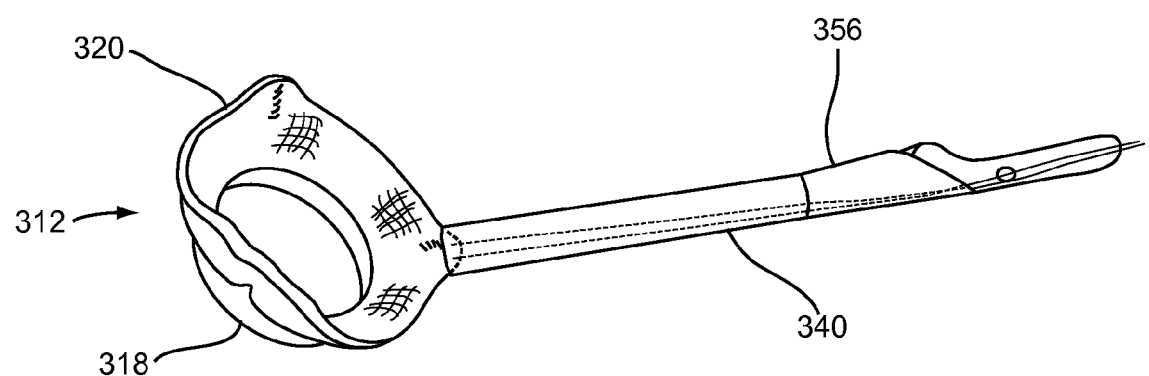

Turning to FIGS. 9A and 9B, in another alternative embodiment, a gasket member 312 and guide shields 356 (one shown for simplicity) may be provided, similar to other embodiments described elsewhere herein, e.g., including an annular ring 318 and sewing cuff 320. Unlike previous embodiments, the guide rails may be constrained in a rolled or other contracted configuration. For example, as shown, a tubular sleeve 340 may be received around at least a portion of the guide rails 356 after rolling, folding, or otherwise reducing the width of the guide rails 356. The sleeve 340 may be substantially flexible and/or transparent, e.g., formed from material similar to the guide shields 356, and may have a length longer or shorter than the guide shields 356.

The sleeve 340 may minimize obstruction caused by the guide shields 356 during introduction, e.g., maximizing access around the gasket member 212, e.g., to deliver fasteners therethrough, and the like. When desired, the sleeve 340 may simply be slid axially from around the guide shields 356, e.g., by pulling an outer end of the sleeves 340 out of the biological annulus. The guide shields 356 may then unroll, unfold, or otherwise open to provide surfaces for guiding and/or facilitating introduction of a valve into the biological annulus towards the gasket member 312. Alternatively, the sleeves 340 may include one or more weakened regions (not shown), e.g., extending axially along the sleeves 340, that may be torn or otherwise separated to facilitate removing the sleeves 340 from around the guide shields 356.

Once the guide shields 356 are opened, the procedure may be completed using any of the methods described herein. Thus, the guide shields 356 may be removed by severing one or more sutures securing the guide shields 356 to the gasket member 312. Alternatively, the guide shields 356 may be slidable from the gasket member 312, e.g., as described above with reference to FIGS. 8A and 8B.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A prosthesis for implanting a valve prosthesis within a biological annulus, comprising:
    an annular prosthesis comprising an annular member implantable within the biological annulus, the annular member being compressible radially inwardly from a relaxed condition to a contracted condition to facilitate delivery into the biological annulus, the annular member being resiliently expandable towards the relaxed condition;

a plurality of elongate leaders extending from the annular prosthesis for guiding a valve prosthesis towards the annular prosthesis; and a plurality of guide shields independent of each other, wherein each guide shield comprises a sheet having an inner surface and an outer surface, wherein the plurality of guide shields are individually, removably attached around a periphery of the annular prosthesis such that the inner surfaces of the sheets of the plurality of guide shields are adapted to define a passage through which a valve prosthesis could be directed towards the annular prosthesis.

2. The prosthesis of claim 1, wherein each of the guide shields comprises a wide base extending partially around a circumference of the annular prosthesis, and a narrow upper end.

3. The prosthesis of claim 2, wherein the wide base of each of the guide shields is removably attached to the annular prosthesis by one or more sutures that may be severed to allow the respective wide base to be separated from the annular prosthesis.

4. The prosthesis of claim 3, wherein the one or more sutures are arranged through holes in the guide shields and the annular prosthesis such that each of the guide shields is removable from the annular prosthesis by cutting only a single cut through the respective one or more sutures.

5. The prosthesis of claim 3, wherein the annular prosthesis comprises one or more anchoring loops for receiving the sutures therethrough such that the sutures are slidable through the anchoring loops when the sutures are severed.

6. The prosthesis of claim 1, wherein the guide shields are slidably attached to the annular prosthesis by one or more tethers such that the guide shields are disposed away from the annular prosthesis and are directable against the annular prosthesis to at least partially define the passage for guiding a valve prosthesis towards the annular prosthesis.

7. The prosthesis of claim 1, wherein the relaxed condition comprises a generally circular shape, and the contracted condition comprises a multiple lobular shape.

8. The prosthesis of claim 1, further comprising:

a valve prosthesis, the leaders being receivable through the valve prosthesis for guiding the valve prosthesis towards the annular prosthesis.

9. The prosthesis of claim 8, wherein the valve prosthesis comprises a plurality of receptacles for slidably receiving respective leaders therethrough.

10. The prosthesis of claim 9, wherein the receptacles and the leaders comprises cooperating connectors for securing the valve prosthesis to the annular prosthesis.

11. The prosthesis of claim 1, wherein the guide shields comprise upper ends, and wherein the upper ends include elements for releasably retaining the leaders to the guide shields to maintain the leaders away from the passage at least partially defined by the guide shields.

12. The prosthesis of claim 11, wherein the elements comprise a slot in the upper end of the guide shields.

13. The prosthesis of claim 1, wherein the guide shields comprise transparent material adapted to allow seeing through the guide shields to locate the annular prosthesis relative to a biological annulus within which the annular prosthesis could be introduced.

14. The prosthesis of claim 1, wherein the plurality of guide shields are adapted for being temporarily extended above the biological annulus at a point during the implantation procedure after the annular prosthesis has already been implanted within the biological annulus.

15. The prosthesis of claim 14, wherein the plurality of guide shields are adapted for being temporarily extended outside of a patient's body at a point during the implantation procedure when the annular prosthesis has already been implanted within the biological annulus.

16. The prosthesis of claim 1, wherein the annular prosthesis defines a plane and a central longitudinal axis extending substantially perpendicular to the plane, and wherein the inner surfaces of the sheets of the plurality of guide shields are configured to face the central longitudinal axis while the outer surfaces of the sheets of the plurality of guide shields are configured to face away from the central longitudinal axis.

17. A heart valve assembly implantable within a biological annulus, comprising:

a first prosthesis comprising an annular member adapted to be implantable within the biological annulus, and a sewing cuff extending outwardly from the annular member;

a second valve prosthesis comprising an annular frame and at least one valve element;

one or more guide shields removably attached to the first prosthesis and extending upwardly therefrom; and a plurality of elongate leaders extending from the first prosthesis, the elongate leaders being configured to slidably engage with the second prosthesis, wherein the elongate leaders extend above the one or more guide shields to guide the second prosthesis toward the one or more guide shields and toward the first prosthesis, wherein the second prosthesis comprises a plurality of receptacles for slidably receiving respective leaders therethrough, and wherein the receptacles and the leaders comprise cooperating connectors for securing the second prosthesis to the first prosthesis.

18. The heart valve assembly of claim 17, wherein the plurality of elongate leaders are adapted for being temporarily extended outside of a patient's body at a point during an implantation procedure after the first prosthesis has already been implanted within the biological annulus.

19. The heart valve assembly of claim 17, wherein the cooperating connectors comprise one or more retention elements on each of the leaders and one or more latches in each of the receptacles for engaging the retention elements when the leaders pass through the receptacles, thereby preventing subsequent removal of the second prosthesis away from the first prosthesis.

20. The heart valve assembly of claim 17, wherein the one or more guide shields comprise a plurality of guide shields, a guide shield being disposed adjacent each of the plurality of leaders.

21. The heart valve assembly of claim 20, wherein the guide shields comprise upper ends, and wherein the upper ends include elements for releasably retaining the leaders to the guide shields to maintain the leaders away from a passage at least partially defined by the guide shields.

22. The heart valve assembly of claim 17, wherein each of the guide shields comprises a wide base extending partially around a circumference of the first prosthesis, and a narrow upper end.

23. The heart valve assembly of claim 17, wherein the one or more guide shields are slidably attached to the first prosthesis by one or more tethers such that each guide shield is disposed away from the first prosthesis and is directable against the first prosthesis to at least partially define a passage for guiding the second prosthesis towards the first prosthesis.

24. The heart valve assembly of claim 23, wherein each of the one or more guide shields is removable from the first prosthesis by pulling an upper end of the guide shield, the tethers sliding freely through the first prosthesis.

25. The heart valve assembly of claim 17, wherein the one or more guide shields comprise transparent material adapted to allow seeing through the one or more guide shields to locate the first prosthesis relative to a biological annulus within which the first prosthesis could be introduced.

26. The heart valve assembly of claim 17, wherein each of the one or more guide shields is removably attached to the first prosthesis by one or more filaments that are capable of being severed to allow the one or more guide shields to be separated from the first prosthesis.

27. The heart valve assembly of claim 17,
wherein the annular member of the first prosthesis defines a plane and a central longitudinal axis extending substantially perpendicular to the plane, and
wherein the plurality of elongate leaders are adapted to be moveable laterally toward or away from the central longitudinal axis.

28. The heart valve assembly of claim 17, wherein the plurality of elongate leaders are comprised of suture materials.

29. A heart valve assembly implantable within a biological annulus, comprising:
a first prosthesis comprising an annular member adapted to be implantable within the biological annulus, and a sewing cuff extending outwardly from the annular member;
a second valve prosthesis comprising an annular frame and at least one valve element; and
one or more guide shields removably attached to the first prosthesis and extending upwardly therefrom, the one or more guide shields being adapted to at least partially defining a passage through which the second prosthesis could be directed towards the first prosthesis,
wherein each of the one or more guide shields comprises a wide base extending partially around a circumference of the first prosthesis, and a narrow upper end,
wherein each wide base is removably attached to the first prosthesis by one or more sutures that may be severed to allow the respective wide base to be separated from the first prosthesis, and
wherein the first prosthesis comprises a plurality of elongate guide rails extending from one of the annular member and the sewing cuff, the guide rails being receivable through the second prosthesis for guiding the second prosthesis towards the first prosthesis.

30. The heart valve assembly of claim 29, wherein the second prosthesis comprises a plurality of receptacles for slidably receiving respective guide rails therethrough.

31. The heart valve assembly of claim 30, wherein the receptacles and the guide rails comprises cooperating connectors for securing the second prosthesis to the first prosthesis.

32. The heart valve assembly of claim 31, wherein the cooperating connectors comprise one or more retention elements on each of the guide rails and one or more latches in each of the receptacles for engaging the retention elements when the guide rails pass through the receptacles, thereby preventing subsequent removal of the second prosthesis away from the first prosthesis.

33. The heart valve assembly of claim 29, wherein the one or more guide shields comprise a plurality of guide shields, a guide shield being disposed adjacent each of the plurality of guide rails.

34. The heart valve assembly of claim 33, wherein the guide shields comprise upper ends, and wherein the upper ends include elements for releasably retaining the guide rails to the guide shields to maintain the guide rails away from the passage at least partially defined by the guide shields.

35. A heart valve assembly implantable within a biological annulus, comprising:
a first prosthesis comprising an annular member adapted to be implantable within the biological annulus, and a sewing cuff extending outwardly from the annular member;
a second valve prosthesis comprising an annular frame and at least one valve element; and
one or more guide shields removably attached to the first prosthesis and extending upwardly therefrom, wherein each of the one or more guide shields is removably attached to the first prosthesis by one or more filaments that are capable of being severed to allow the one or more guide shields to be separated from the first prosthesis,
wherein each of the one or more guide shields comprises a sheet having an inner surface and an outer surface, and
wherein the one or more guide shields extend around a circumference of the first prosthesis such that the inner surface of each of the respective sheets of the one or more guide shields at least partially defines a passage through which the second valve prosthesis could be directed towards the first prosthesis after the first prosthesis has been implanted within the biological annulus.

36. The heart valve assembly of claim 35, wherein the one or more guide shields comprise transparent material adapted to allow seeing through the one or more guide shields to locate the first prosthesis relative to a biological annulus within which the first prosthesis could be introduced.

37. The heart valve assembly of claim 35, wherein the one or more guide shields are adapted such that the second prosthesis slidably contacts the inner surface of each of the respective sheets of the one or more guide shields, but does not contact the outer surface of each of the respective sheets of the one or more guide shields, when the second prosthesis is directed towards the first prosthesis.

38. The heart valve assembly of claim 35,
wherein the annular member of the first prosthesis defines a plane and a central longitudinal axis extending substantially perpendicular to the plane, and
wherein the inner surface of each of the respective sheets of the one or more guide shields is configured to face the central longitudinal axis while the outer surface of each of the respective sheets of the one or more guide shields is configured to face away from the central longitudinal axis.

* * * * *